(12) United States Patent
Riojas et al.

(10) Patent No.: US 11,723,738 B2
(45) Date of Patent: Aug. 15, 2023

(54) SURGICAL DEVICE TIP WITH DEFLECTABLE JOINT

(71) Applicants: Vanderbilt University, Nashville, TN (US); University of Tennessee Research Foundation, Knoxville, TN (US)

(72) Inventors: Katherine E. Riojas, Nashville, TN (US); Robert J. Webster, Nashville, TN (US); Daniel Caleb Rucker, Knoxville, TN (US); Kaitlin Oliver Butler, Knoxville, TN (US); Ryan Ponten, Issaquah, WA (US)

(73) Assignees: UNIVERSITY OF TENNESSEE RESEARCH FOUNDATION, Knoxville, TN (US); VANDERBILT UNIVERSITY, Nashville, TN (US)

( * ) Notice: Subject to any disclaimer, the term of this patent is extended or adjusted under 35 U.S.C. 154(b) by 705 days.

(21) Appl. No.: 15/804,146

(22) Filed: Nov. 6, 2017

(65) Prior Publication Data
US 2019/0133705 A1 May 9, 2019

(51) Int. Cl.
*A61B 34/00* (2016.01)
*A61B 34/32* (2016.01)
(Continued)

(52) U.S. Cl.
CPC ............ *A61B 34/72* (2016.02); *A61B 1/0052* (2013.01); *A61B 1/0055* (2013.01);
(Continued)

(58) Field of Classification Search
None
See application file for complete search history.

(56) References Cited

U.S. PATENT DOCUMENTS

| 4,195,623 A * | 4/1980 | Zeff ...................... A61M 1/106 |
| | | 417/384 |
| 7,090,683 B2 * | 8/2006 | Brock ................ A61B 17/0469 |
| | | 606/1 |

(Continued)

OTHER PUBLICATIONS

Philip J. Swaney et al., "Design, Fabrication, and Testing of a Needle-Sized Wrist for Surgical Instruments", Journal of Medical Devices, vol. 11, Mar. 2017.

(Continued)

*Primary Examiner* — Catherine M Voorhees
*Assistant Examiner* — Elizabeth K So
(74) *Attorney, Agent, or Firm* — Tarolli, Sundheim, Covell & Tummino L.L.P.

(57) ABSTRACT

A small diameter surgical tool implements an agonist-antagonist deflectable joint. The deflectable joint is an actuatable bendable structure that uses push-pull, agonist-antagonist action of a pair of nested tubes to actuate the joint. The tubes are designed to have non-central, offset neutral axes, and they are fixed together at locations distal to the deflectable joint, such as at their distal ends. Axial translations of the tubes relative to each other causes a push-pull, agonist-antagonist action between the tubes, which causes the deflectable joint to bend. In one implementation, a deflectable joint can be created in nested tubes by configuring radial portions of the tube sidewalls extending along the joint to have an axial region of reduced stiffness. As a result, axial agonist-antagonist motion between the tubes can cause bending of the deflectable joint.

36 Claims, 21 Drawing Sheets

(51) Int. Cl.
    *A61M 25/01*     (2006.01)
    *A61B 1/005*     (2006.01)
    *A61B 34/30*     (2016.01)
    *A61M 25/00*     (2006.01)
    *A61B 1/05*     (2006.01)

(52) U.S. Cl.
    CPC ............ *A61B 1/0057* (2013.01); *A61B 34/30* (2016.02); *A61B 34/32* (2016.02); *A61M 25/0147* (2013.01); *A61B 1/05* (2013.01); *A61B 2034/301* (2016.02); *A61B 2034/306* (2016.02); *A61M 25/0054* (2013.01); *A61M 25/0113* (2013.01); *A61M 25/0136* (2013.01); *A61M 25/0138* (2013.01); *A61M 2025/0004* (2013.01); *A61M 2025/006* (2013.01); *A61M 2025/015* (2013.01); *A61M 2205/0266* (2013.01)

(56) References Cited

U.S. PATENT DOCUMENTS

| | | | |
|---|---|---|---|
| 7,374,553 B2* | 5/2008 | Koerner | A61B 18/02 604/95.04 |
| 7,878,984 B2* | 2/2011 | Jacobsen | A61M 25/0013 600/585 |
| 7,998,112 B2* | 8/2011 | Chow | A61M 25/0012 604/528 |
| 8,414,598 B2* | 4/2013 | Brock | A61B 34/71 606/130 |
| 8,708,953 B2* | 4/2014 | Salahieh | A61B 1/00135 604/95.01 |
| 9,211,160 B2* | 12/2015 | Pivotto | A61B 34/74 |
| 2004/0138529 A1 | 7/2004 | Wiltshire et al. | |
| 2008/0243064 A1 | 10/2008 | Stahler et al. | |
| 2011/0087314 A1* | 4/2011 | Diederich | A61N 7/022 607/113 |
| 2011/0238083 A1 | 9/2011 | Moll et al. | |
| 2016/0346513 A1* | 12/2016 | Swaney | A61B 17/3417 |

OTHER PUBLICATIONS

Peter A. York et al., "A Wrist for Needle-Sized Surgical Robots", 2015 IEEE International Conference on Robotics and Automation (ICRA), May 2015.
Kaitlin Oliver-Butler et al., "Concentric Agonist-Antagonist Robots for Minimally Invasive Surgeries", Proceedings vol. 10135, Medical Imaging 2017:Image Guided Procedures, Robotic Interventions, and Modeling, Mar. 2017.

* cited by examiner

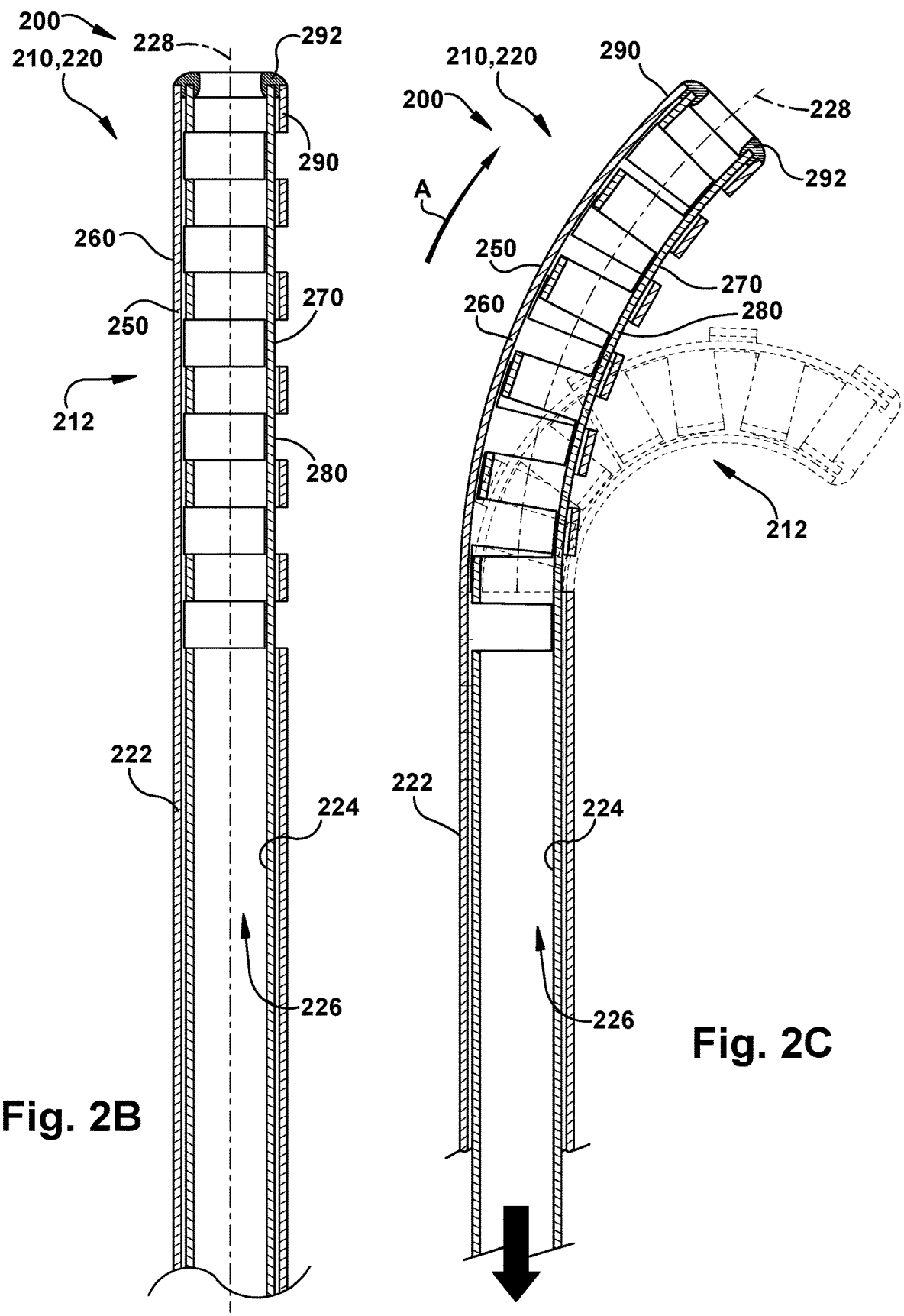

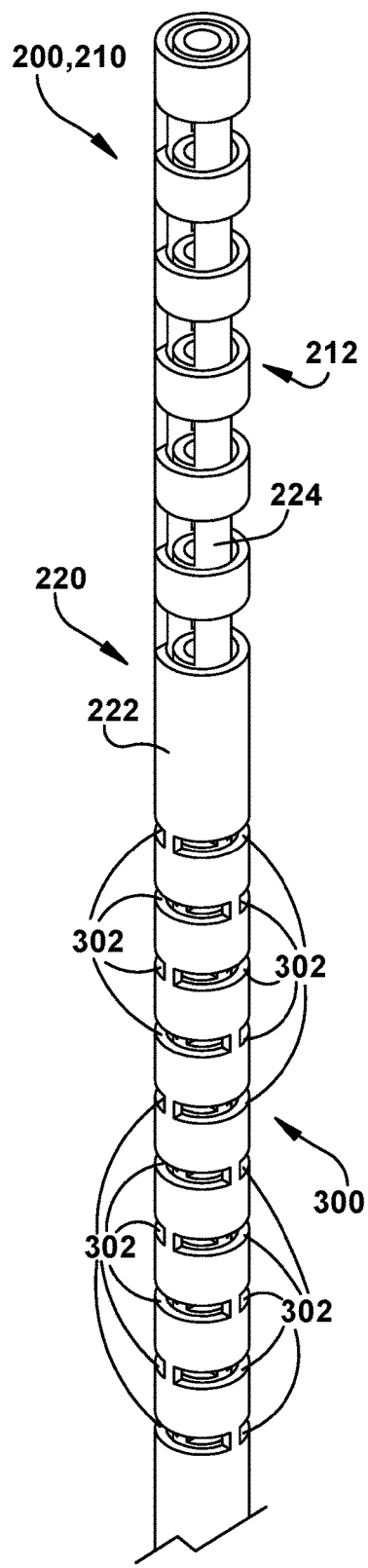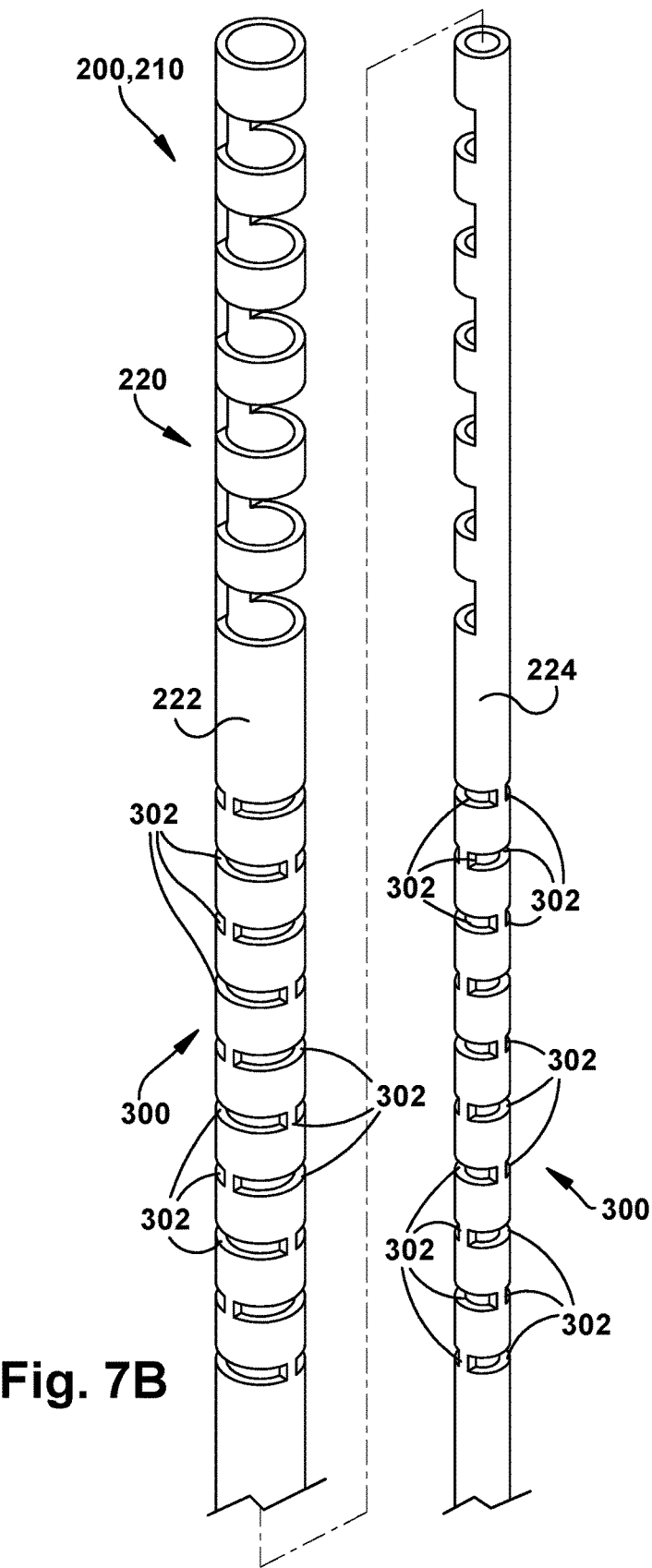
Fig. 7A
Fig. 7B

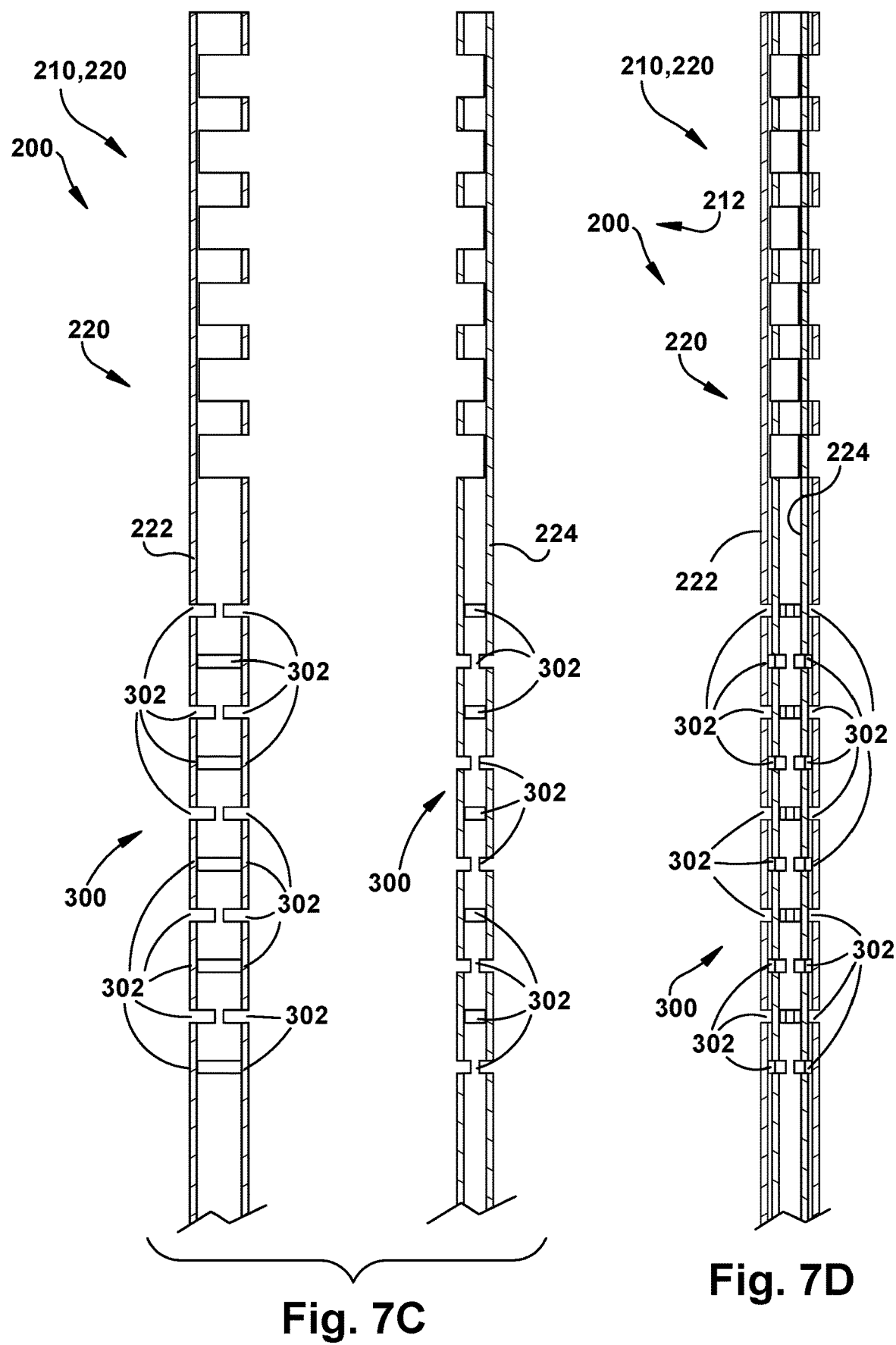

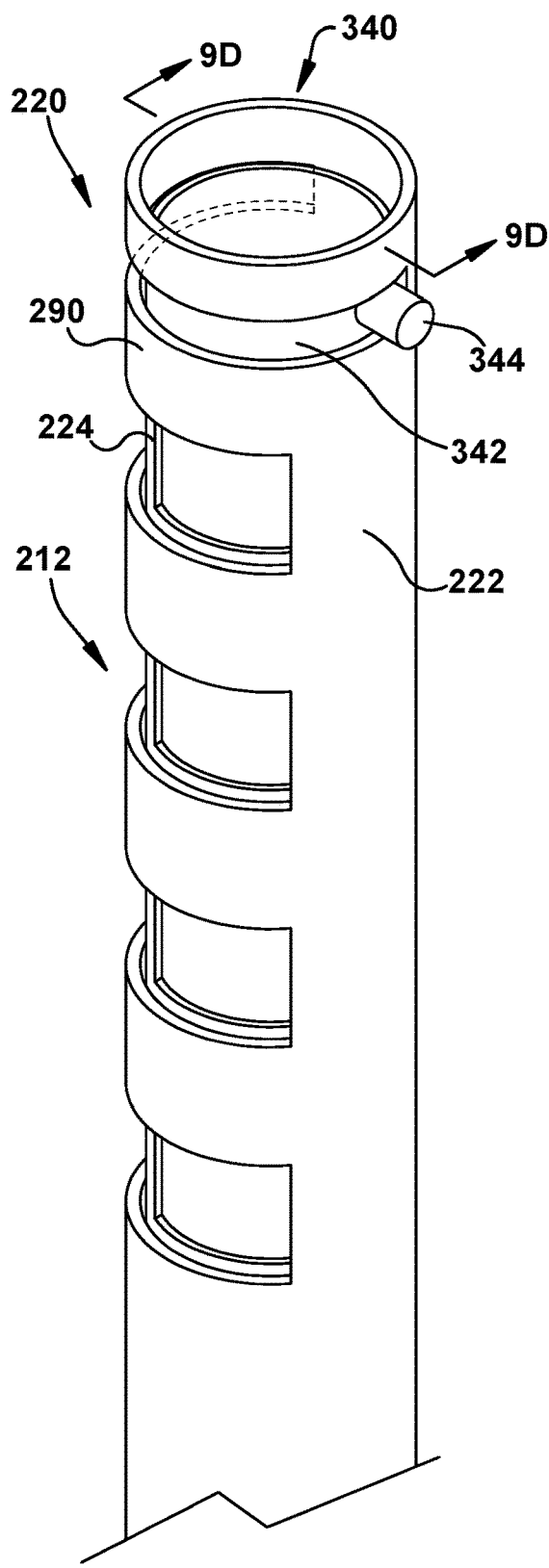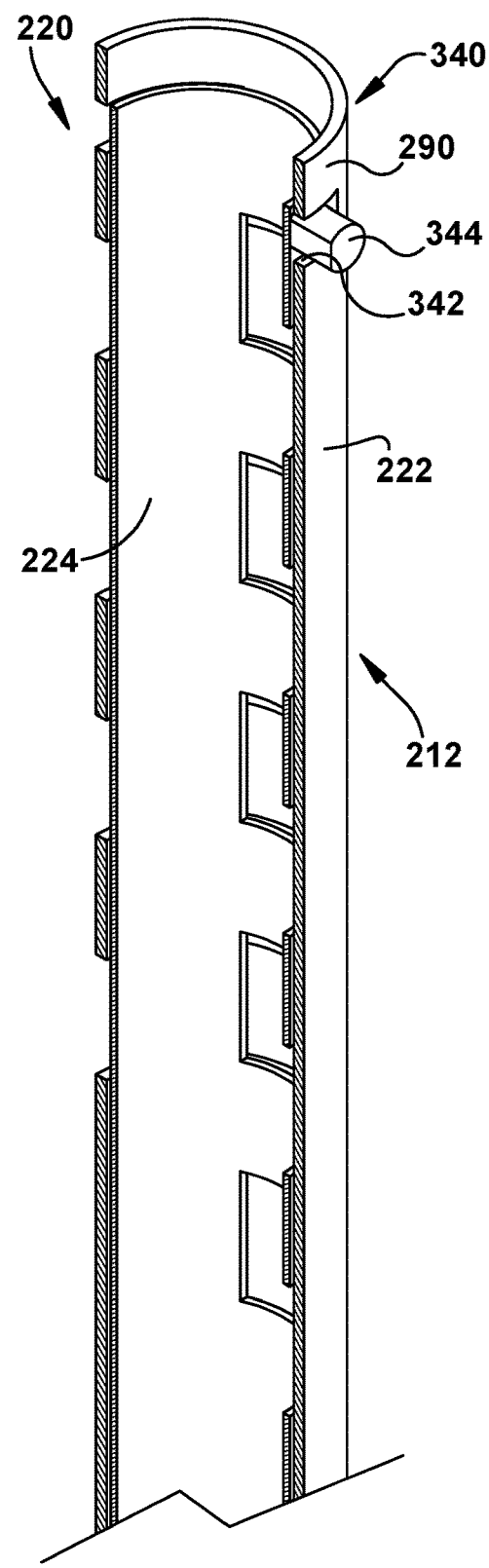
Fig. 9C
Fig. 9D

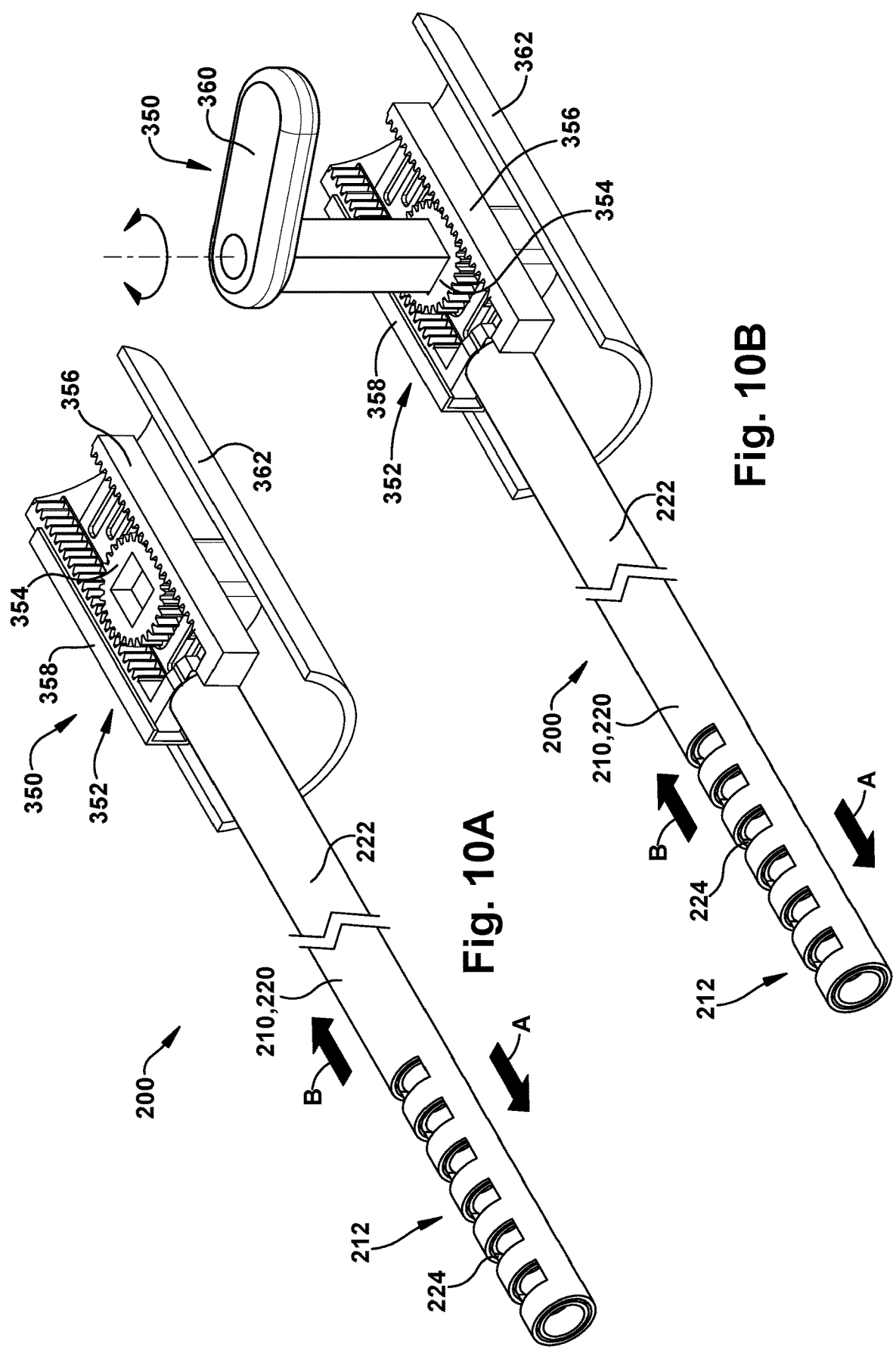

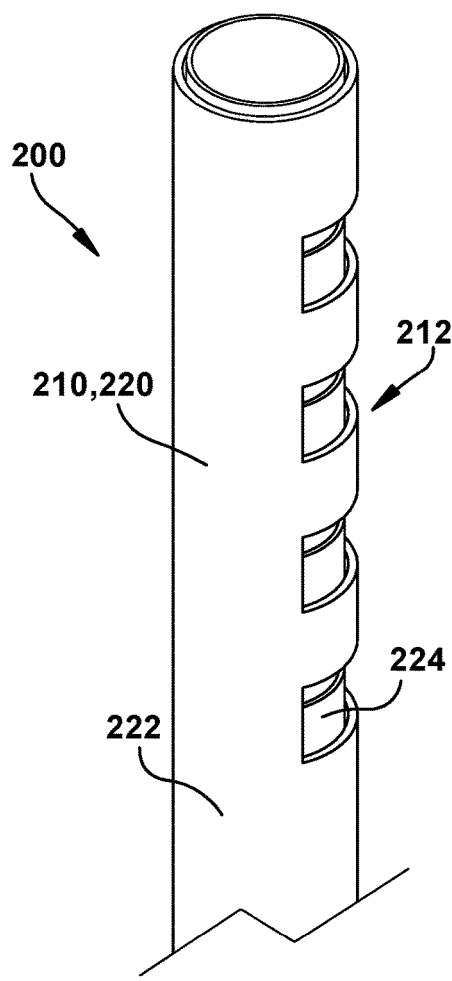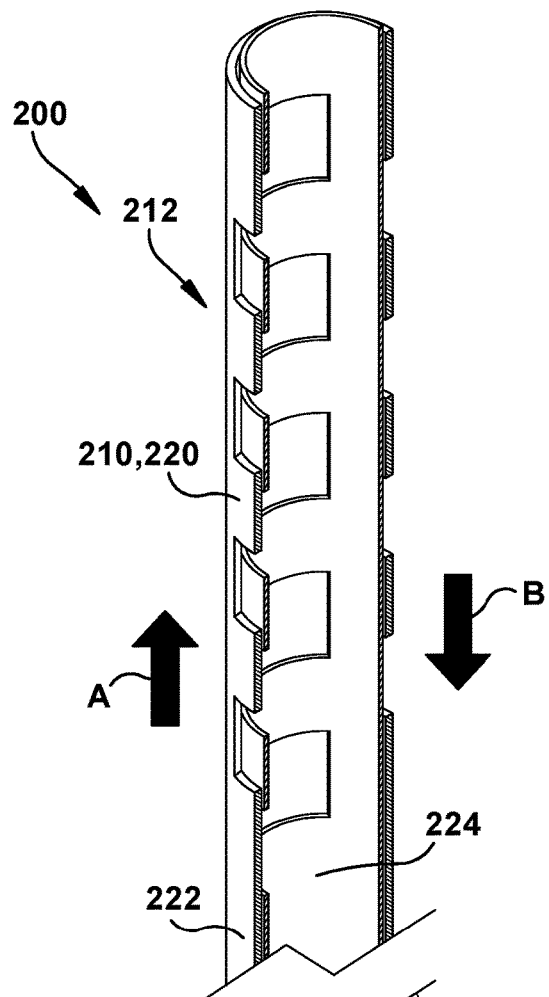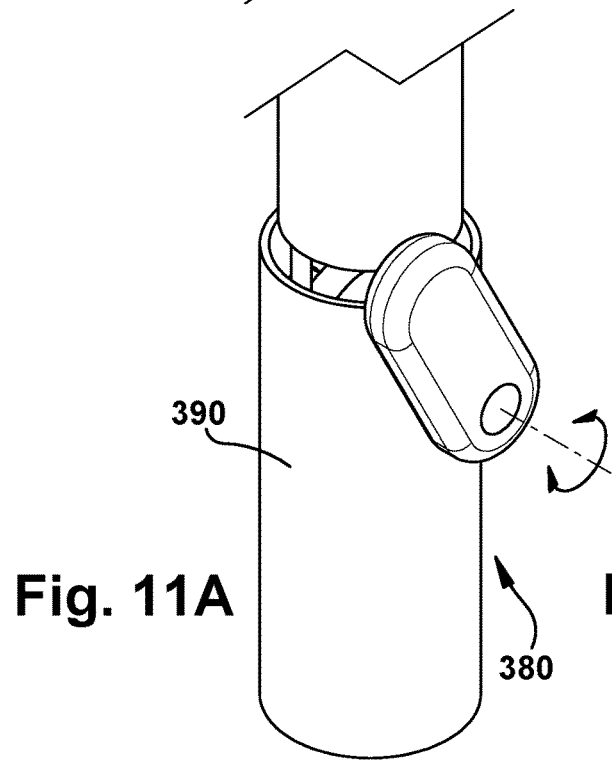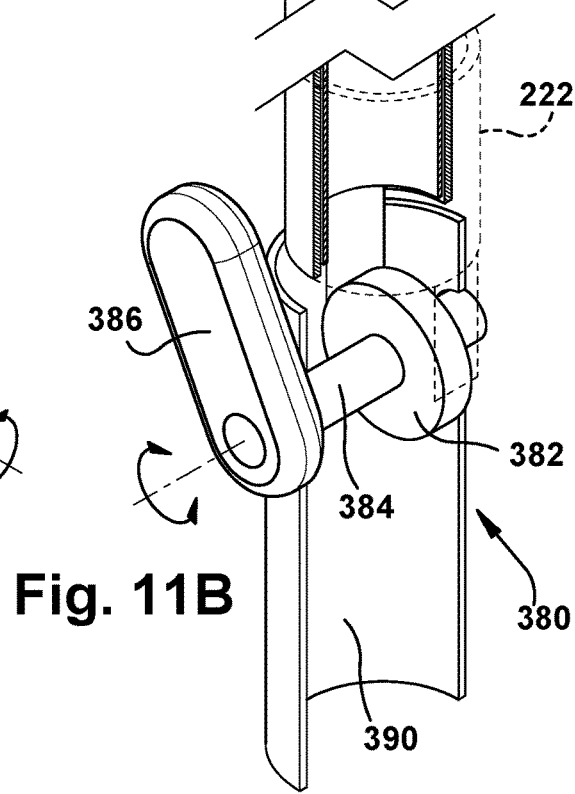
Fig. 11A  Fig. 11B

SURGICAL DEVICE TIP WITH DEFLECTABLE JOINT

GOVERNMENT FUNDING This invention was made with government support under grant number DC014037 awarded by the National Science Foundation. The government has certain rights in the invention.

GOVERNMENT RIGHTS

This work was funded in part by the National Science Foundation (NSF) under CMMI-1427122, and a Graduate Research Fellowship. The U.S. Government may have certain rights to the invention.

FIELD OF THE INVENTION

The present invention relates to surgical tools for performing surgical operations. More specifically, the present invention relates to small diameter surgical tools for navigating the patient's anatomy in order to deliver therapy to a target location in the patient's body. In particular, the present invention relates to a deflectable joint for providing dexterity in these small diameter surgical tools.

BACKGROUND

There is a pressing need in robotic or remotely controlled hand-operated surgery for small-diameter surgical tools with deflectable joints at various positions along the length of the tool, such as at the tip of the tool or at discrete locations along the length of the tool. These tools can be especially useful in procedures involving dexterity driven tasks, such as tissue dissection, resection, and suturing. Delivered through a natural orifice or percutaneously directly, through a delivery device such as an endoscope, or through the lumen of another small diameter surgical tool, these small-diameter surgical tools can be extremely useful in delicate and intricate surgical procedures, such as colorectal resection, pituitary tumor resection, neurosurgery, and intracardiac surgery. Many other surgical procedures can be aided by these tools.

SUMMARY

An agonist-antagonist deflectable joint can be implemented in a small diameter surgical tool. The agonist-antagonist deflectable joint is an actuatable bendable structure that uses push-pull, agonist-antagonist action of a pair of nested tubes to actuate the joint. The tubes are designed to have non-central, offset neutral axes, and they are fixed together at locations distal to the deflectable joint, such as at their distal ends. Axial translations of the tubes relative to each other causes the push-pull, agonist-antagonist action between the tubes, which causes the deflectable joint to bend. In one implementation, a deflectable joint can be created in nested tubes by configuring radial portions of the tube sidewalls extending along the joint to have an axial region of reduced stiffness. As a result, axial agonist-antagonist motion between the tubes can cause bending of the deflectable joint.

According to this agonist-antagonist configuration, when the tubes exert axial push/pull forces on each other, which is realized at the connection between the tubes, e.g., at the distal end. As a result, for the tube upon which the pulling force is exerted, the section of the tube along the deflectable joint will bend in the direction of the axial region of reduced sidewall stiffness. Since the tubes are nested, the other tube will follow this bend. It is through this agonist-antagonist, push-pull action between the tubes that the deflectable joint can be actuated to bend.

One particular manner in which the tubes can be made to have a reduced stiffness along the bend joint is by selectively cutting asymmetric cutouts or notches into the profile of the tubes. The notches relocate the neutral bending planes of the tubes away from the center of the inner lumen of the nested tube structure. This relocation causes the tubes to bend in response to the agonist-antagonist relative axial movement of the tubes.

Because of this unique push-pull, agonist-antagonist configuration, the bendable structure does not present elastic stability issues, and offers a large range of motion and a low overall stiffness. Additionally, by varying the position of the neutral axes along the length of each tube (by configuring the position, direction, size, shape, etc. of the axial region of reduced sidewall stiffness), variable curvature actuation modes can be achieved. Pre-curving the nested tubes can additionally increase the workspace of a single segment. A single two-tube assembly can be used to create a deflectable structure with three degrees-of-freedom (DOF). Assemblies of three or more tubes can provide additional degrees-of-freedom. Additionally, multiple nested-tube surgical tool devices with deflectable portions can be deployed in a nested configuration to provide added dexterity.

According to one aspect, a surgical apparatus includes a nested tube structure including a first tube including a tubular side wall and a deflectable portion in which a portion of the side wall is configured to have a stiffness that is lower than opposing portions. The apparatus also includes a second tube including a tubular side wall and a deflectable portion in which a portion of the side wall is configured to have a stiffness that is lower than opposing portions. The apparatus further includes a connection between the first and second tubes at a location that is distal of the deflectable portions. The first tube is positioned so that the deflectable portions are at least partially aligned with each other axially, and so that the low stiffness portions face in radial directions that differ angularly from one another.

According to another aspect, alone or in combination with any other aspect, the deflectable portions of the first and second tubes can define a deflectable joint that is actuatable to bend in two or more directions.

According to another aspect, alone or in combination with any other aspect, the first and second tubes can be configured such that the application of an axial pulling force on the first tube relative to the second tube causes the first tube to pull on the second tube at the connection, which causes the deflectable portion of the second tube to deflect and bend in the direction of the low stiffness portion of the second tube. The first and second tubes can also be configured such that the application of an axial pushing force on the first tube relative to the second tube causes the second tube to pull on the first tube at the connection, which causes the deflectable portion of the first tube to deflect and bend in the direction of the low stiffness portion of the first tube.

According to another aspect, alone or in combination with any other aspect, the tubes can be configured so that the bending of the deflectable portion of the second tube in response to the pulling by the first tube exerts a bending force on the deflectable portion of the first tube, which causes the deflectable portion of the first tube to bend in the direction of the bend in the second tube.

According to another aspect, alone or in combination with any other aspect, the tubes can be configured so that the bending of the deflectable portion of the first tube in response to the tension applied by the second tube exerts a bending force on the deflectable portion of the second tube, which causes the deflectable portion of the second tube to bend in the direction of the bend in the first tube.

According to another aspect, alone or in combination with any other aspect, the tubes can be configured so that the axial pulling force on the first tube relative to the second tube can be applied by one or both of a) applying a pulling force on the first tube relative to the second tube, and b) by applying a pushing force on the second tube relative to the first tube. The tubes can also be configured so that the axial pushing force on the first tube relative to the second tube can be applied by one or both of c) applying a pulling force on the second tube relative to the first tube, and d) by applying a pushing force on the first tube relative to the second tube.

According to another aspect, alone or in combination with any other aspect, the surgical apparatus can also include an inner lumen that extends the length of the nested tube structure and is configured to receive a surgical instrument.

According to another aspect, alone or in combination with any other aspect, the surgical instrument can include an additional nested tube structure including a first tube and a second tube including deflectable portions that together define a deflectable joint actuatable to bend in opposite directions.

According to another aspect, alone or in combination with any other aspect, the surgical instrument can include at least one of curettes, grippers, surgical lasers, graspers, retractors, scissors, imaging tips, cauterizing tips, ablation tips, morcelators, knives/scalpels, cameras, irrigation ports, suction ports, needles, probes, and manipulators.

According to another aspect, alone or in combination with any other aspect, the first tube and the second tube can be nitinol tubes.

According to another aspect, alone or in combination with any other aspect, the first tube and the second tube can have one of a round and polygonal cross-section.

According to another aspect, alone or in combination with any other aspect, the surgical apparatus can also include a surgical instrument connected to a distal end of the nested tube structure.

According to another aspect, alone or in combination with any other aspect, the surgical instrument can include at least one of curettes, grippers, surgical lasers, graspers, retractors, scissors, imaging tips, cauterizing tips, ablation tips, morcelators, knives/scalpels, cameras, irrigation ports, suction ports, needles, probes, and manipulators.

According to another aspect, alone or in combination with any other aspect, the surgical apparatus can include a control handle connected to the nested tube structure, the control handle including an actuator mechanism for actuating the deflectable joint.

According to another aspect, alone or in combination with any other aspect, the actuator mechanism can include a lever that is pivotable to move the first tube axially relative to the second tube.

According to another aspect, alone or in combination with any other aspect, the actuator mechanism can include a gear and rack mechanism including a central gear rotatable manually via a handle and first and second rack gears engaged with the central gear and movable in opposite directions in response to rotation of the central gear, wherein the first rack gear is connected to the second tube and the second rack gear is connected to the first tube, and wherein rotation of the central gear via the handle moves the first and second tubes axially in opposite directions relative to each other.

According to another aspect, alone or in combination with any other aspect, the actuator mechanism can include a central wheel supported on an axle and rotatable manually via a handle connected to the axle, wherein the second tube and the first tube are connected to an outer surface of the wheel at different circumferential positions, wherein rotation of the wheel via the handle moves the first and second tubes axially in opposite directions relative to each other.

According to another aspect, alone or in combination with any other aspect, the actuator mechanism can include a clutch that decouples the control handle from the nested tube structure so that the control handle can be rotated relative to the nested tube structure.

According to another aspect, alone or in combination with any other aspect, the nested tube structure can also include an additional nested tube that further defines the deflectable joint. The additional tube can reinforce one of the first and second tubes. The additional tube can include a deflectable portion in which a portion of the side wall is configured to have a stiffness that is lower than opposing portions of the side wall that at least partially align with the bendable portion of at least one of the first and second tubes.

According to another aspect, alone or in combination with any other aspect, the nested tube structure can also include an additional nested tube that further defines the deflectable joint. The additional tube can include a deflectable portion in which a portion of the side wall is configured to have a stiffness that is lower than opposing portions of the side wall and a distal end connected to at least one of the first and second tubes.

According to another aspect, alone or in combination with any other aspect, the deflectable portion of the additional tube can be at least partially aligned with the deflectable portion of at least one of the first and second tubes. The deflectable portion of the additional tube can be actuatable to bend in the direction of the low stiffness portion of the additional tube.

According to another aspect, alone or in combination with any other aspect, the application of an axial pulling force on the additional tube relative to at least one of the first and second tubes can cause the deflectable portion of the additional tube to deflect and bend in the direction of the low stiffness portion of the additional tube.

According to another aspect, alone or in combination with any other aspect, the tubes can be configured such that the low stiffness portion of the additional tube is rotated relative to the low stiffness portions of the first and second tubes so that the bending plane of the deflectable portion of the additional tube bends is different than the bending planes of the deflectable portions of the first and second tubes.

According to another aspect, alone or in combination with any other aspect, the cutouts of the first tube can face in at least two different directions and the cutouts of the second tube can face in at least two different directions, wherein the deflectable joint when actuated bends in at least two different directions that coincide with the directions of the cutouts.

According to another aspect, alone or in combination with any other aspect, the low stiffness portion of the first tube can be formed by portions removed from the tubular sidewall of the first tube to form a plurality of cutouts. The low stiffness portion of the second tube can be formed by portions removed from the tubular sidewall of the second tube to form a plurality of cutouts.

According to another aspect, alone or in combination with any other aspect, the cutouts of the first tube and second tube can have depths that increase progressively from proximally to distally so that the bend of the deflectable portion becomes progressively sharp proximally to distally.

According to another aspect, alone or in combination with any other aspect, the cutouts of the first tube and second tube can have depths that decrease progressively from proximally to distally so that the bend of the deflectable portion becomes progressively sharp distally to proximally.

According to another aspect, alone or in combination with any other aspect, the radial positions of the cutouts of the first tube and second tube can rotate progressively from proximally to distally.

According to another aspect, alone or in combination with any other aspect, the surgical apparatus can also include a bearing tip at the distal end of the nested tube structure. The bearing tip can include a first bearing component connected to the first tube and a second bearing component connected to the second tube. The first and second bearing components are connected to each other and have a bearing interface that promotes free rotation of the bearing components and the attached tubes while fixing their relative axial positions.

According to another aspect, alone or in combination with any other aspect, the surgical apparatus can also include a pinned tip connection at the distal end of the nested tube structure. The pinned tip can include a slot in the second tube and a pin that is fixed to the first tube and projects radially outward through the slot. The pin and slot can interface each other to permit relative rotational movement of the first tube and the second tube while fixing their relative axial positions.

According to another aspect, alone or in combination with any other aspect, the first and second tubes each can also include a flexible transmission segment positioned proximally of the deflectable joint. The transmission segment of each tube can include a series of low stiffness regions of the first and second tubes that promote free bending with minimal impact on axial strength and torsional stiffness.

According to another aspect, alone or in combination with any other aspect, the low stiffness regions of the first and second tubes can be formed by a plurality of slits that extend laterally into the tubes.

According to another aspect, alone or in combination with any other aspect, the slits can extend into the first and second tubes in pairs that extend toward each other into opposing sides of their respective tubes. Adjacent pairs of slits can be rotated ninety degrees relative to each other about a longitudinal axis of the tubes.

According to another aspect, alone or in combination with any other aspect, the position of the transmission segment can be configured to coincide with the location of a bend or a bendable portion of a structure through which the nested tube structure is delivered.

DRAWINGS

FIGS. 2A-2D illustrate the configuration and operation of the bendable tip configuration of FIGS. 1A and 1B.

FIGS. 7A-7E illustrate a variation on the concentric tube structure of FIGS. 1A and 1B including a flexible transmission section.

FIGS. 9A-9D illustrate variations on the concentric tube structure of FIGS. 1A and 1B including different tip support structures.

FIGS. 10A and 10B illustrate a control handle for the concentric tube structure.

FIGS. 11A and 11B illustrate another control handle for the concentric tube structure.

DESCRIPTION

Figures 1A, 1B:
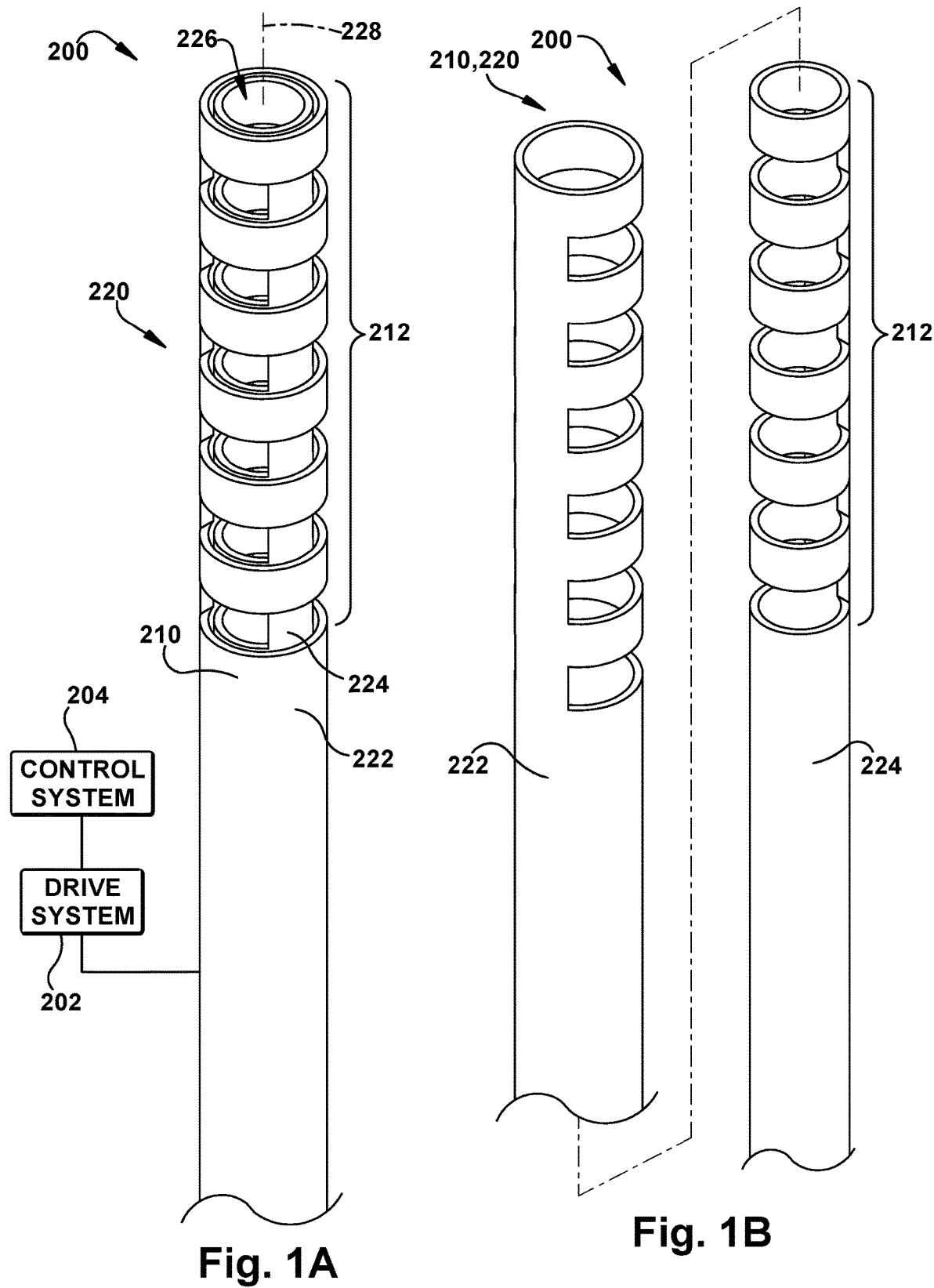
FIGS. 1A and 1B illustrate a concentric tube structure implementing another small diameter bendable tip configuration.

Referring to FIGS. 1A and 1B, according to an example configuration, a surgical system 200 includes a surgical apparatus or tool 210 having a small-diameter tubular form factor and including a bendable or deflectable joint 212. As described herein, the deflectable joint 212 is configured to operate in an agonist-antagonist manner such that the joint can be actuated to deflect/bend in different, e.g., opposite, directions relative to a central axis 228 of the surgical tool 210. In the example configuration of FIGS. 1A and 1B, the deflectable joint 212 forms a distal tip of the surgical tool 210 and therefore can be referred to herein as a deflectable tip 212. The position of the deflectable joint 212, however, is not limited and could be located at any location along the length of the surgical tool 210.

In the example configuration of FIGS. 1A and 1B, the surgical tool 210 includes one or more small-diameter actuatable agonist-antagonist deflectable tube devices 220 including two or more tubes configured to translate and/or rotate relative to each other. The deflectable tube device 220 can be configured for robotic operation or manual operation. As shown in FIGS. 1A and 1B, the surgical system 200 can include a drive system 202 for mechanically actuating the deflectable tube device 220, and a control system 204 for controlling the operation of the drive system.

In a robotic implementation, the drive system 202 can include various actuation components, such as motors, solenoids, actuators, linkages, drive mechanisms, transmissions, etc. that supply the motive forces for operating the deflectable tube device 220. In the robotic implementation, the control system 204 can include the input (operator control signals), processing, and signal generating components that generate the drive signals for controlling operation of the actuation components of the drive system 202. In a manual implementation, the drive system 202 can be mechanism(s) that, through manual operation (i.e., by hand), manipulate the concentric tubes of the deflectable tube device 220. As such, the control system 204 would be replaced by the user, such as a surgeon, manually operating the drive system 204.

Each deflectable tube device 220 includes two or more tubes. In the example configuration of FIGS. 1A and 1B, the deflectable tube device includes an outer tube 222 and an inner tube 224. In this example configuration, an inner lumen 226 of the device 220 is defined by the lumen of the inner tube 224 and extends the length of the device through the deflectable tip 212. The deflectable tip 212 is formed by distal portions of the outer and inner tubes 222, 224. The outer tube 222 and inner tube 224 are both constructed of a flexible material, such as nitinol tubing. Other flexible materials, such as plastics, could also be used to construct the tubes 222, 224. The outer tube 222 and inner tube 224 are configured to be movable both axially along and rotationally about the longitudinal central axis 228 of the surgical tool 212.

In this description, the central axis 228 of the deflectable tube device 220 follows approximately the centers of the concentric tubes 222, 224. Since the tubes 222, 224 are flexible/bendable, the central axis 228 is considered to follow whatever bend the concentric tubes follow. In this description, when reference is made to rotating the tubes 222, 224 about the axis 228, it is meant that rotation imparted to the tubes 222, 224 at one location on the tubes, such as at the interface with the drive system 202, causes the remainders of the tubes to rotate about the axis, regardless of whether the axis follows a curved or straight path.

In this description, when reference is made to translating the tubes 222, 224 along the axis 228, it is meant that translation is imparted to the tubes 222, 224 at one location on the tubes, such as at the interface with the drive system 202, and the remainders of the tubes translate along the axis, regardless of whether the axis follows a curved or straight path. Additionally, those skilled in the art will appreciate that the central axis may not follow both tubes exactly through a curve, as they may shift radially and/or laterally due to tolerances and spacing between the tubes. For this reason, the notion that the central axis 228 follows both tubes 222, 224 can be considered to be somewhat generalized.

The deflectable portion 212 of the device 220 is illustrated in FIGS. 2A-D. In this example configuration, the deflectable portion 212 is a distal tip of the device 220. As shown in these figures, the deflectable joint 212 includes a deflectable portion 250 of the outer tube 222 and a deflectable portion 270 of the inner tube 224. In the deflectable tip configuration of FIGS. 19 and 20, the deflectable portions 250, 270 are distal tip portions of the tubes 222, 224.

Figure 2A:
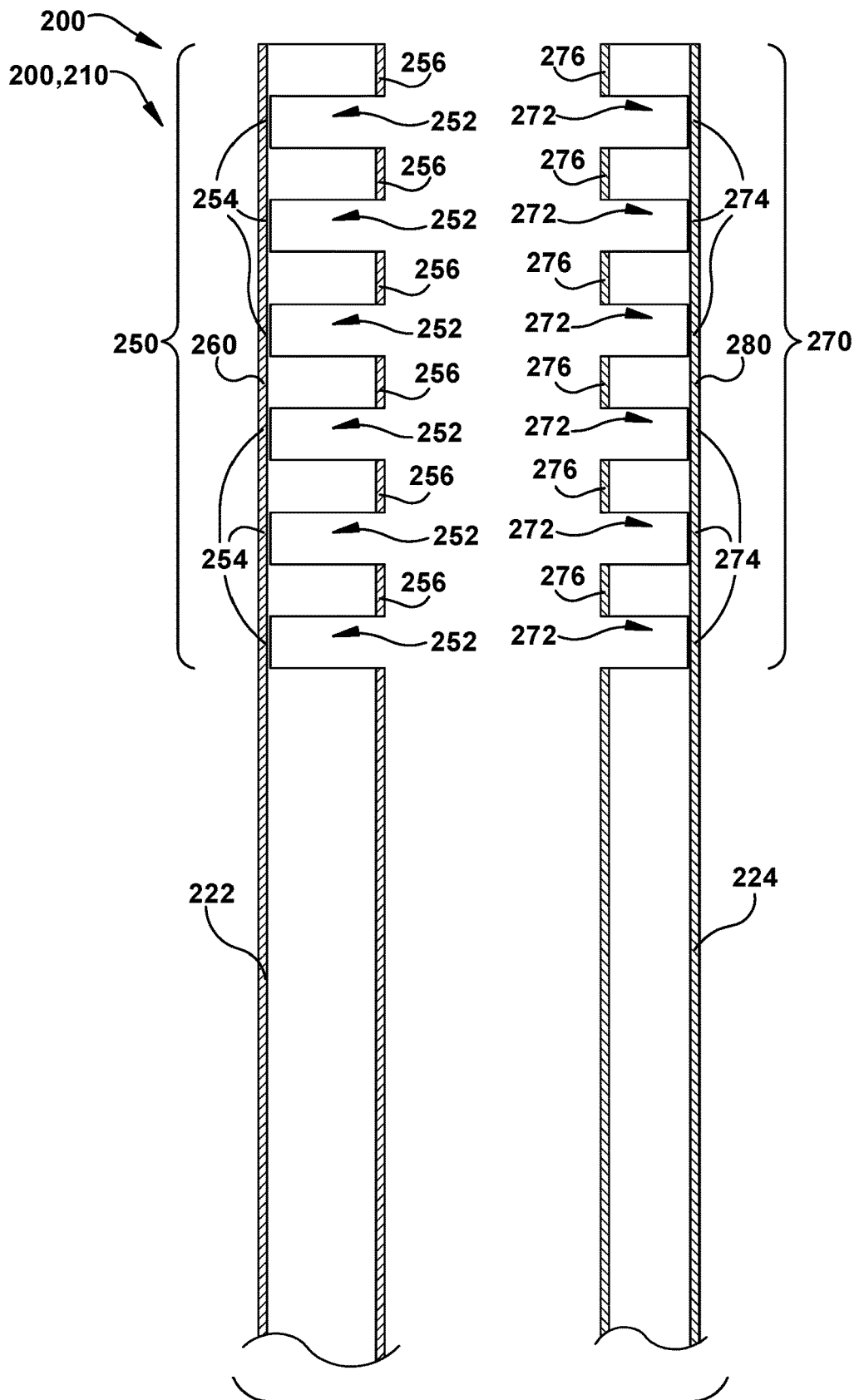

The deflectable tip 212 has a non-actuated condition, shown in FIG. 2B, in which the deflectable tip is not bent and extends essentially or substantially along the tool axis 228. The deflectable tip 212 is configured for bi-directional bending along a bending plane which coincides with the section plane of the sectional views of FIGS. 2A-D. The tip 212 has a first actuated condition, shown in FIG. 2C, in which the tip is deflected in a first direction (see arrow A) to bend in the bending plane and assume a curved configuration. The tip 212 can be deflected in the first direction to an extreme, which is shown in dashed lines in FIG. 2C.

Figure 2D:
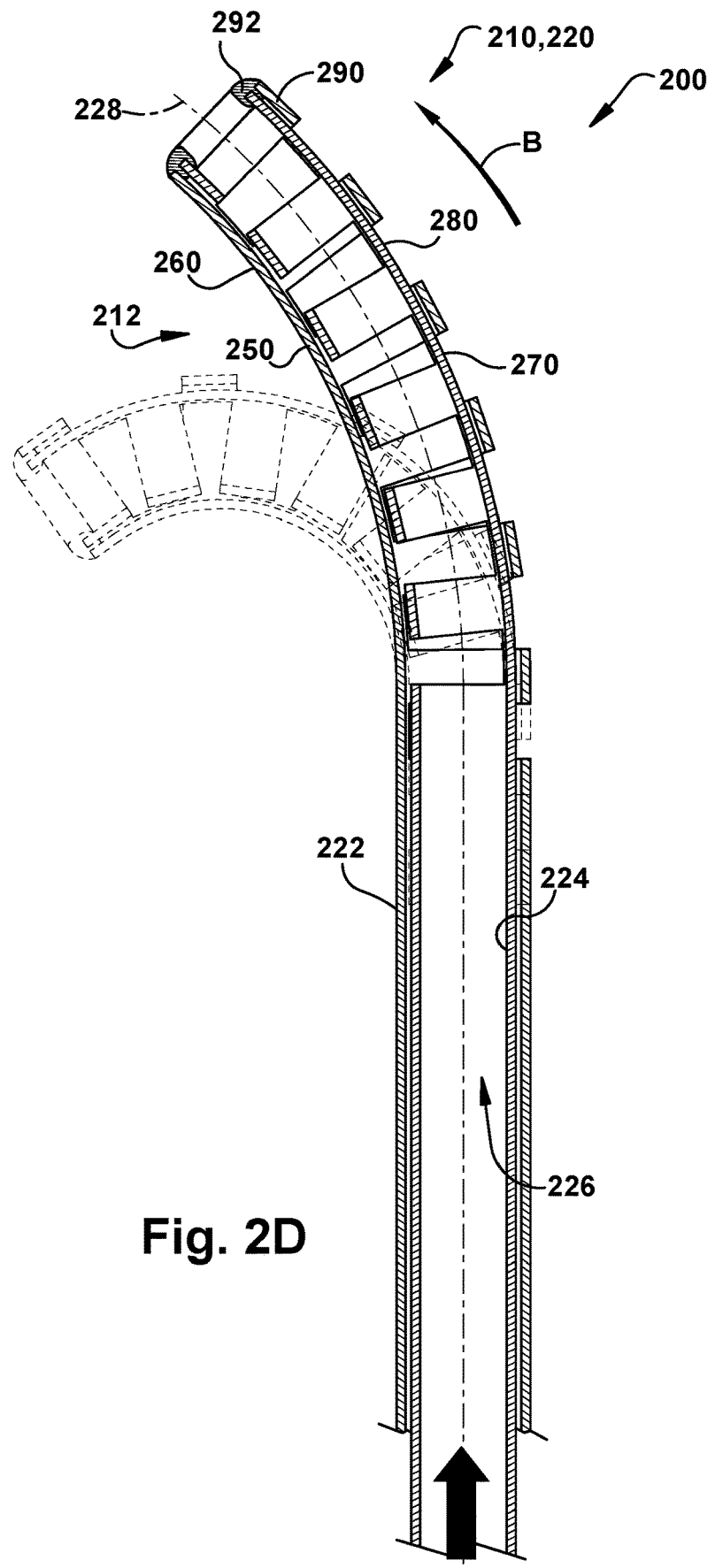

The deflectable tip 212 has a second actuated condition, shown in FIG. 2D, in which the tip is deflected in a second direction (see arrow B), opposite the first direction (arrow A), to bend in the bending plane and assume a curved configuration. The tip 212 can be deflected in the first direction to an extreme, which is shown in dashed lines in FIG. 2D. The deflectable tip 212 is selectively actuatable so that the degree of bending in the first and second directions can be set to any position between the extremes shown in dashed lines in FIGS. 2C-D.

The deflectable portion 250 of the outer tube 222 has a configuration in which one side of the tube has a region of reduced stiffness relative to the other side of the tube in order to offset the neutral axis of the cross section away from the lumen centerline. This helps facilitate the actuatable deflection of the deflectable tip 212. To achieve this purpose, in the example configurations illustrated herein, the outer tube 222 has a notched configuration. Referring to FIG. 2A, the reduced stiffness of the deflectable portion 250 is formed by a series of cutouts 252 where tube material (e.g., nitinol) is removed from the outer tube 222. The cutouts 252 define bend joints 254, which are the portions of the outer tube 224 that remain after the removal of the cutout material. The cutouts 252 also define bend sections 256, which are tube segments that extend between the bend joints 254. In the example configuration illustrated in FIG. 2A, the deflectable portion 250 of the outer tube 222 includes six cutouts 252 that define six bend joints 254 and six bend sections 256. The deflectable portion 250 could include a greater number of cutouts 252 or fewer cutouts.

Similarly, the deflectable portion 270 of the inner tube 224 has a configuration in which one side of the tube has a region of reduced stiffness relative to the other side of the tube in order to offset the neutral axis of the cross section away from the lumen centerline. This helps facilitate the actuatable deflection of the deflectable tip 212. To achieve this purpose, in the example configurations illustrated herein, the inner tube 224 has a notched configuration. Referring to FIG. 2A, the reduced stiffness of the deflectable portion 270 is formed by a series of cutouts 272 where tube material (e.g., nitinol) is removed from the inner tube 224. The cutouts 272 define bend joints 274, which are the portions of the outer tube 224 that remain after the removal of the cutout material. The cutouts 272 also define bend sections 276, which are tube segments that extend between the bend joints 274. In the example configuration illustrated in FIG. 2A, the deflectable portion 270 of the inner tube 224 includes six cutouts 272 that define six bend joints 274 and six bend sections 276. The deflectable portion 270 could include a greater number of cutouts 272 or fewer cutouts.

In the example configuration of FIGS. 2A-2D, the design parameters for each of the deflectable portions 250, 270 of the tubes 222, 224 include the diameters of the tubes, the cut depth of the cutouts 252, 272, the axial length of the cutouts, the axial length of the bend sections 256, 276, the number of cutouts, and the shape or geometry of the cutouts. Through careful selection of these design parameters, the performance characteristics of the deflectable tip 212, such as bending stiffness, arc length, bend radius, axial strength, and torsional stiffness can be selected.

Those skilled in the art will appreciate that the reduced stiffnesses of the tubes 222, 224 to form the deflectable portions 250, 270 can be achieved in manners other than through the implementation of the cutouts 252, 272. For example, in a plastic implementation, selective stiffening can be achieved through the use of different plastic materials to form the opposite sides of the tubes 222, 224. This can also be achieved through material variations within the cross section of the tubes 222, 224, or by varying the wall thicknesses of the tubes.

The notched configuration of the deflectable portions 250, 270 permit the deflectable portions to bend. For the outer tube 222, as the deflectable portion 250 bends, the bend joints 254 deflect and the bend sections 256 move and rotate/pivot. This movement is blocked when adjacent bend sections 256 engage each other or, in the case of the most proximally located bend section, engage the remainder of the outer tube 222. The degree of movement that each bend section 256 is permitted to undergo is thus defined and limited by the aforementioned design parameters for the deflectable portion 250 of the outer tube 222.

For the inner tube 224, as the deflectable portion 270 bends, the bend joints 274 deflect and the bend sections 276 move and rotate/pivot. This movement is blocked when adjacent bend sections 276 engage each other or, in the case of the most proximally located bend section, engage the remainder of the inner tube 224. The degree of movement that each bend section 276 is permitted to undergo is thus defined and limited by the aforementioned design parameters for the deflectable portion 270 of the inner tube 224.

Referring to FIGS. 2B-D, when assembled to form the deflectable tube device 220 and the deflectable tip 212, the inner tube 224 and outer tube 222 are positioned so that their respective cutouts 252, 272 are aligned with each other axially and are positioned facing in radially opposite (i.e., 180-degree) directions. Arranged in these positions, at a distal tip 290 of the of the deflectable tube device 220, a connection 292 connects the outer tube 222 to the inner tube 224. This connection 292 can be mechanical (e.g., one or more pins or fasteners), adhesive (e.g., a glue, epoxy, or tape), a bonding (e.g., ultrasonic weld, heat bond), or a fixture, such as a cap.

The connection 292 locks the tips of the tubes 222, 224 together, thus preventing translational movement of the interconnected tube ends relative to each other along the axis 228. The connection 292 also can prevent rotational movement of the interconnected tube ends relative to each other about the axis 228. In certain configurations, however (see, e.g., FIGS. 9A-9D), the connection 292 can permit relative rotation of the tubes 222, 224 about the axis 228. It is this connection 292 that facilitates actuation of the deflectable tip 212 without the use of cables, wires, or any other actuation member extending inside or outside the lumen 226 of the device 220.

Advantageously, the bend joints 254 of the deflectable portion 250 of the outer tube 222 are aligned with each other linearly/axially and are interconnected by their co-adjacent bend sections 256. Likewise, the bend joints 274 of the deflectable portion 270 of the inner tube 224 are aligned with each other linearly/axially and are interconnected by their co-adjacent bend sections 276. In this manner, the interconnected bend joints 254 and bend sections 256 of the outer tube 222 form a spline 260 that extends continuously along the deflectable portion 250 and allows tension to be applied by the inner tube 224 along its entire length. Similarly, the interconnected bend joints 274 and bend sections 276 of the inner tube 224 form a spline 280 that extends continuously along the deflectable portion 270 and allows tension to be applied by the outer tube 222 along its entire length. Together, the splines 260, 280 permit the tubes 222, 224 to apply either tension or compression along their lengths, which allows for actuating the deflectable tip 212 in the first and second directions (see FIGS. 2C-D) in response to relative axial movement of the tubes creating a push-pull on each other.

Actuation of the deflectable tip 212 is effectuated through relative axial movement of the tubes 222, 224, in an agonist-antagonist manner in which relative axial movements of the tubes act against each other to cause the tip to deflect. This agonist/antagonist action between the tubes is described herein as push/pull action of the tubes. For ease of explanation, the actuation is described herein in terms of pushing or pulling on the inner tube 224 to move the inner tube axially relative to the outer tube 222. Those skilled in the art will appreciate that the same effect can be realized by pushing or pulling on the outer tube 222 to move the outer tube axially relative to the inner tube 224. In fact, relative axial movement of the tubes 222, 224 can also be realized by pushing on one tube while pulling on the other tube. All of these push/pull methods yield the same result. It is for these reasons that the agonist-antagonist operation of the deflectable tube device 220 and the deflectable tip 212 is described in terms of push/pull on the inner tube 224, with the understanding that push/pull on the inner tube can be achieved by push/pull on one or both of the inner and outer tubes.

Referring to FIG. 2C, pulling the inner tube 224 relative to the outer tube 222 (as indicated generally by the downward facing arrow) actuates the deflectable tip 212 to bend in the first direction (arrow A) toward the illustrated bend condition. When this occurs, the inner tube 224, through the spline 280, pulls on or applies tension to the distal tip 290 at the connection 292 of the outer tube 222 and inner tube 224. The inner tube 224 pulling on the outer tube 222 causes the bend joints 254 of the outer tube to deflect or bend in the first direction toward the region of reduced stiffness of the deflectable portion 270, i.e., away from the spline 260 and toward the cutouts 252. During this bending, the cutouts 252 provide space for the bend sections 256 to move toward each other. As a result, the outer tube 222 bends in the first direction.

The bending of the deflectable portion 250 of the outer tube 222 causes the deflectable portion 270 of the inner tube 224 to bend along with it. Since the bend joints 274 of the inner tube 224 are at least partially aligned with the bend joints 254 of the outer tube 222, the deflectable portions 250, 270 bend with each other with relatively little resistance. As a result, pulling on the inner tube 224 causes the deflectable tip 212 to bend in the first direction. The axial distance that the inner tube 224 is pulled relative to the outer tube 222 determines the degree to which the deflectable tip 212 bends in the first direction. With enough pull on the inner tube 224, the deflectable tip 212 can be placed in the fully deflected first condition 212'.

Conversely, referring to FIG. 2D, pushing the inner tube 224 relative to the outer tube 222 (as indicated generally by the upward facing arrow) actuates the deflectable tip 212 to bend in the second direction (arrow B) toward the illustrated bend condition. When this occurs, the inner tube 224 pushes on the distal tip 290 at the connection 292 of the tubes 222, 224. In effect, the outer tube 222, through the spline 260, pulls on the distal tip of the inner tube 224. This pulling on the inner tube 224 causes the bend joints 274 of the inner tube to deflect or bend in the second direction toward the region of reduced stiffness of the deflectable portion 250, i.e., away from the spline 280 and toward the cutouts 272. During this bending, the cutouts 272 provide space for the bend sections 276 to move toward each other. As a result, the inner tube 224 bends in the second direction.

The bending of the deflectable portion 270 of the inner tube 224 causes the deflectable portion 250 of the outer tube 222 to bend along with it. Since the bend joints 254 of the outer tube 222 are at least partially aligned with the bend joints 274 of the inner tube 224, the deflectable portions 250, 270 bend with each other with relatively little resistance. As a result, pulling on the outer tube 222 causes the deflectable tip 212 to bend in the second direction. The axial distance that the outer tube 222 is pulled relative to the inner tube 224 determines the degree to which the deflectable tip 212 bends in the second direction. With enough pull on the outer tube 222, the deflectable tip 212 can be placed in the fully deflected second condition 212".

Alternative Tubular Cross-Sectional Configurations

Figures 3A, 3B:
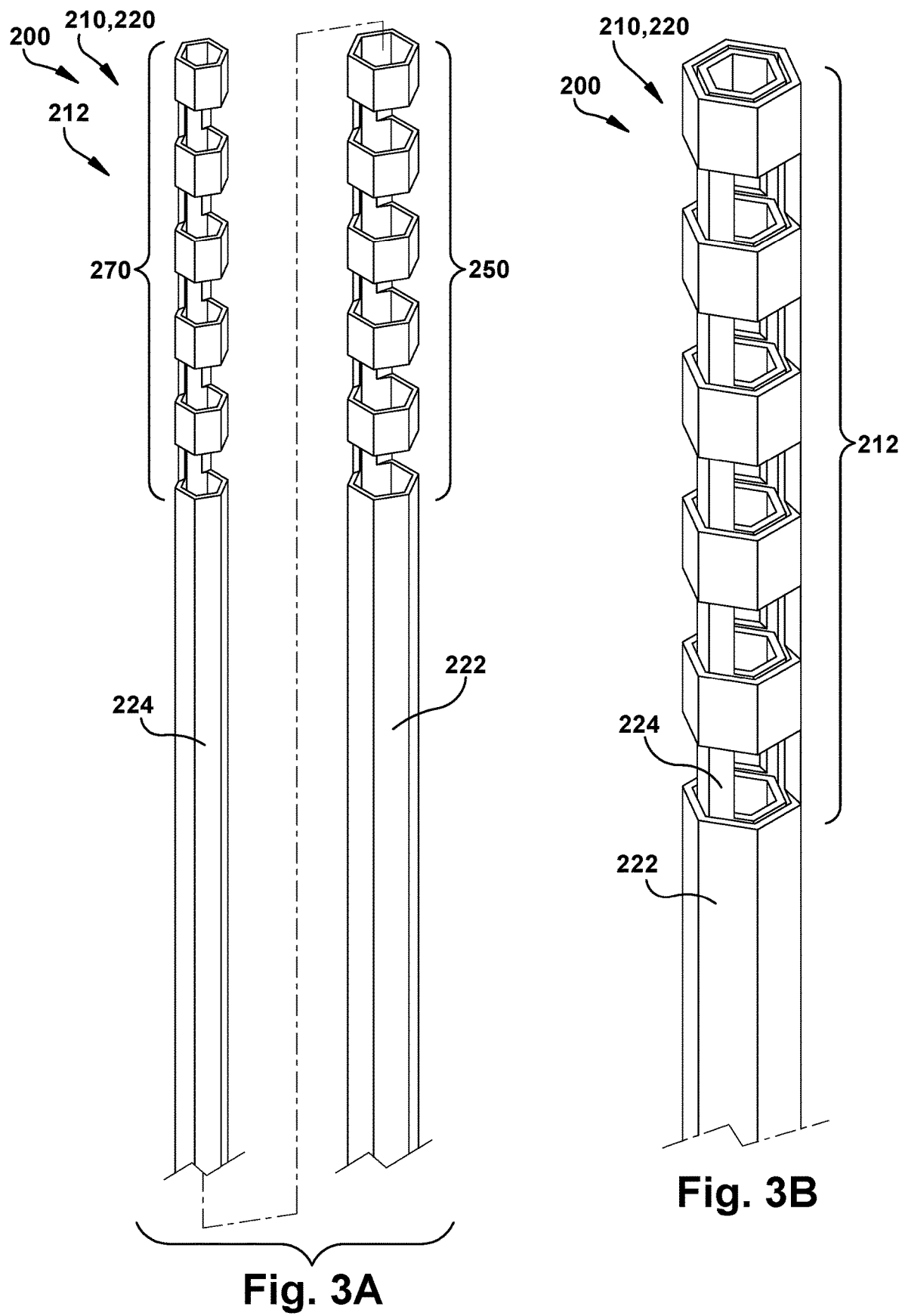
FIGS. 3A and 3B illustrate a variation on the cross-section of the concentric tube structure.

The inner and outer tubes of the deflectable tube device 220 can have cross-sectional configurations other than the round cross-section illustrated in FIGS. 2A-2D. Referring to FIGS. 3A and 3B, the surgical system 200 can include a surgical tool 210 in the form of a deflectable tube device 220 that includes an inner tube 224 and an outer tube 222, each of which has a hexagonal cross-sectional configuration. The deflectable tube device 220 thus has a hexagonal cross-sectional configuration. Alternative cross-sectional shapes, such as octagonal or other polygonal cross-sectional shapes, or elliptical cross-sectional shapes, can also be implemented.

Figure 4A:
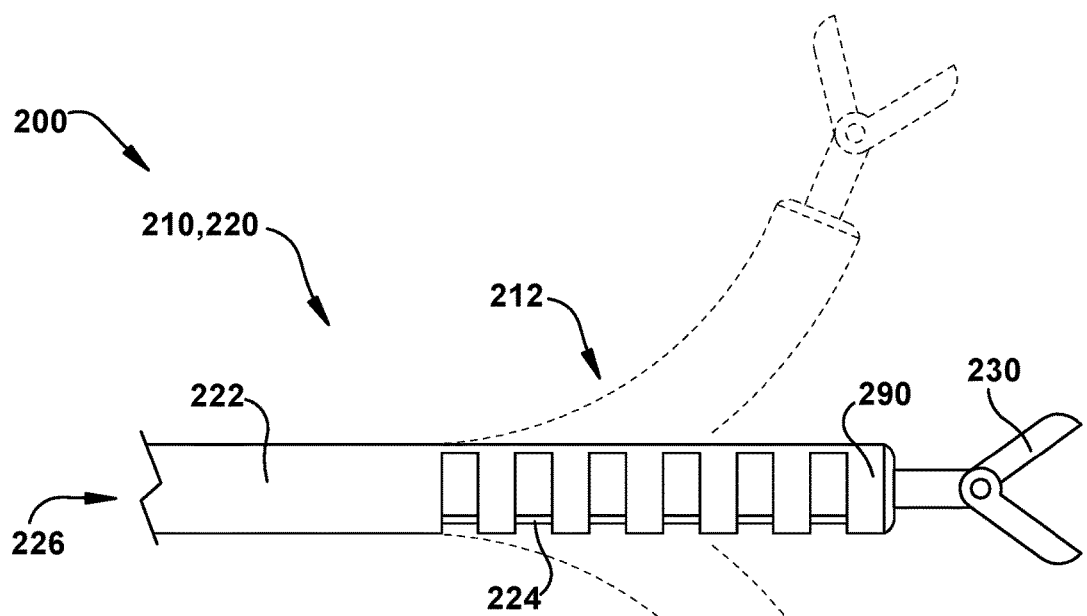
FIGS. 4A and 4B illustrate different tool implementations for the concentric tube structure and bendable tip.

In operation, the deflectable tube device 220, particularly the deflectable tip 212, can operate in a push/pull to actuate manner that is similar or identical to that described above in regard to the circular cross-section configuration of FIGS. 2A-D. Any non-circular cross-sectional configuration of the device 220 can provide certain performance characteristics that may be desirable over those provided by a circular cross-section. For example, the hexagonal cross-section of the device 220 of FIGS. 3A and 3B can have a higher torsional stiffness or bending resistance than a similarly dimensioned device with a circular cross-section, because the cross sections cannot rotate with respect to each other. Implementations The surgical tool 210 can be configured to utilize the deflectable tube device 220 in a variety of manners. For example, as shown in FIG. 4A, the surgical tool 210 can utilize the deflectable tube device 220 as an actuatable sheath in which the device/tool can be delivered to a surgical site, e.g., via endoscope (straight or flexible), cannula (straight or flexible), or directly without using an introductory device. Once delivered, actuating the deflectable tip 212 in combination with gross rotational and axial positioning of the deflectable tube device 220 can position the distal end 290 in a precise location at the surgical site. Since the configuration of the distal tip 212 is such that actuator tendon wires are not required, the inner lumen 226 of the device 220 is left open and clear to deliver one or more surgical instruments, such as one or more additional deflectable tube devices, a deflectable tube device carrying a surgical tool, or one or more surgical tools carried by wire or other structures. Example surgical instruments include curettes, grippers, surgical lasers, graspers, retractors, scissors, imaging tips, cauterizing tips, ablation tips, morcelators, knives/scalpels, cameras, irrigation ports, suction ports, needles, probes, manipulators or any other surgical instrument.

In this configuration of the surgical tool 210, the distal tip 290 of the deflectable tube device 220 is delivered to the surgical site. Then, the surgical instrument is navigated through the lumen 226 of the device 220 and delivered to the surgical site. The surgical instrument is then operated separately to perform the desired operation. The operation of the surgical instrument can, however, be aided through actuation of the deflectable tube device 220 in concert with the instrument.

Figure 4B:
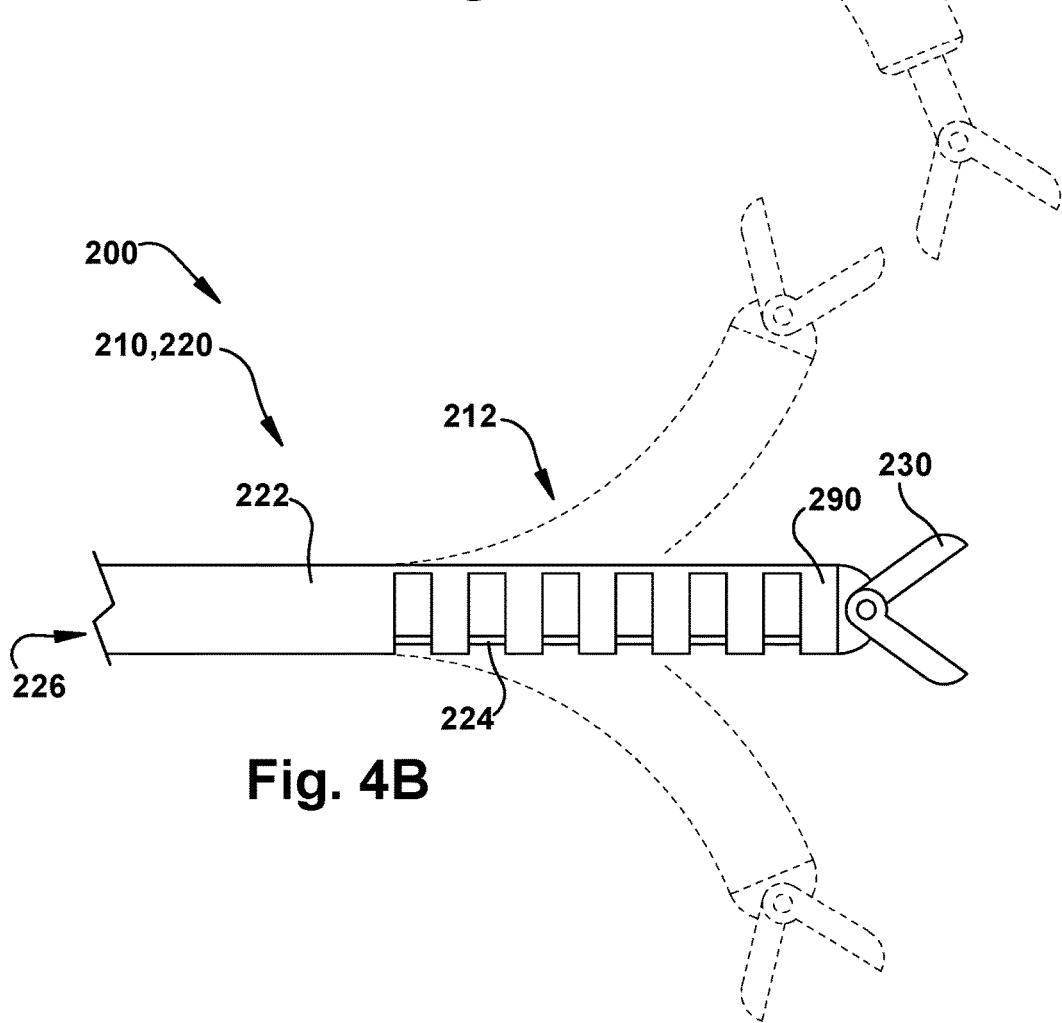

As another example, as shown in FIG. 4B, the surgical tool 210 can itself carry an end effector or instrument 230 connected to the distal end 290 of the deflectable tube device 220 and operated either remotely or through manipulation via the deflectable tube device. The end effector 230 can be any surgical instrument for which delivery via the small diameter surgical tool 210 is desired. For example, the end effector 230 can be a curette, grippers, surgical lasers, graspers, retractors, scissors, imaging tips, cauterizing tips, ablation tips, morcelators, knives/scalpels, cameras, irrigation ports, suction ports, needles, probes, manipulators or any other suitable surgical instrument.

In this configuration of the surgical tool 210, the deflectable tube device 220 can deliver the end effector 230 to a desired surgical location in a variety of manners. For example, the deflectable tube device 220 can deliver the end effector 230 via an endoscope (straight or flexible) a catheter (straight or flexible), or even directly without using an introductory device. In one particular implementation, the tubes 222, 224 of the device 220 can form the innermost tubes of a deflectable tube robotic structure having at least one additional concentric outer tube. In this implementation, the deflectable tip 212 and end effector 230 can be delivered via this deflectable tube robotic structure, which itself can be delivered via an endoscope, catheter, or directly, as set forth above.

The end effector 230 is connected to the distal end 290 of the deflectable tube device 220 at the distal end of the deflectable tip 212. The deflectable tip 212 can thus manipulate the end effector 230 through manipulation of the device 220 and deflection of the tip 212. Advantageously, the deflectable tube device 220, particularly the deflectable tip 212, is configured so that actuation of the tip does not require the use of any cables, wires, or any other element that extends through the inner lumen 226 of the device. This leaves the lumen 226 open and available for any other purpose, such as providing an electrical, mechanical, or fluid connection with the end effector 230, providing an irrigation or suction channel, facilitating the use of a camera, or a combination of these purposes.

The surgical tool 210 can implement the principles of the deflectable tube device 220 and its deflectable joint 212 configuration in a variety of manners. In its simplest form, the deflectable joint 212 can be implemented as a deflectable tip 212 of a deflectable tube device 220, as shown and described in FIGS. 1A-2D. In this configuration, the device 220 has three degrees of freedom: gross translational movement of the device along the axis 228, gross rotational movement of the device about the axis, and bi-directional bending of the deflectable tip 212. As mentioned previously, the deflectable joint 212 can be located at any position along the length of the device 220. The degrees of freedom, however, remain the same: translation, rotation, and bending.

Pre-Curvature to Shape Workspace

The inner tube 224 and outer tube 222 of the deflectable tube device 220 can be constructed of a material that facilitates a pre-curvature of the tubes themselves or the deflectable joint 212. For example, a shape memory alloy, such as a nickel-titanium ("nitinol") alloy, can be bent to a desired curved configuration and heated so that the alloy retains or "remembers" this curvature. This is shown in FIG. 5A.

Figure 5A:
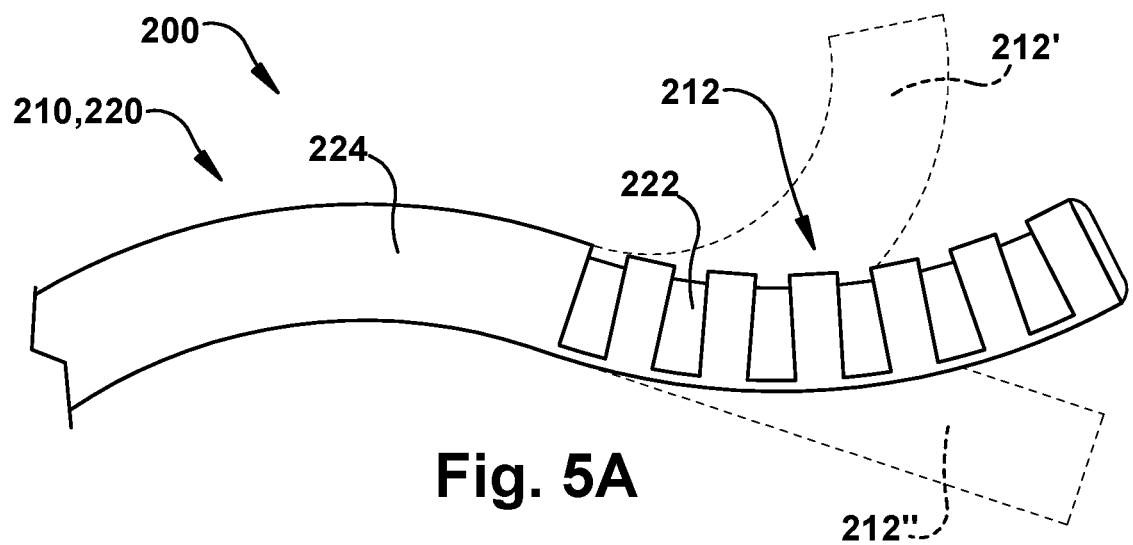
FIGS. 5A-5D illustrate different tip configurations for the small diameter bendable tip.

In FIG. 5A, the deflectable tip 212 has a pre-curved configuration, with the unactuated condition illustrated in solid lines. The deflectable tip 212 is actuatable in the manner described for bi-directional movement from the pre-curved configuration. In the pre-curved configuration, actuation of the first direction can act to further curve the deflectable tip, as illustrated in dashed lines at 212'. Actuation in the second direction can act to extend or straighten the curvature of the deflectable tip, as illustrated in dashed lines at 212".

Advantageously, the pre-curvature of the deflectable tip 212 can permit the distal tip 290 to reach further in the bending plane in the first direction. This further reach, of course, comes at the cost of a lesser reach in the bending plane in the second direction. The pre-curvature shifts the workspace of the of the deflectable tube device 220. It will therefore be appreciated that the workspace of the surgical tool 210 can be tailored to a specific workspace, anatomy, and procedure.

Cutout Designs

The curvature of the deflectable joint 212 at any point along the joint is influenced by characteristics of the cutouts 252, 272, such as their location, depth, and angular position. By varying the configurations of the cutouts 252, 272, the direction and magnitude of curvature in the bending plane at any point on the deflectable joint 212 can be dictated.

Figure 5B:
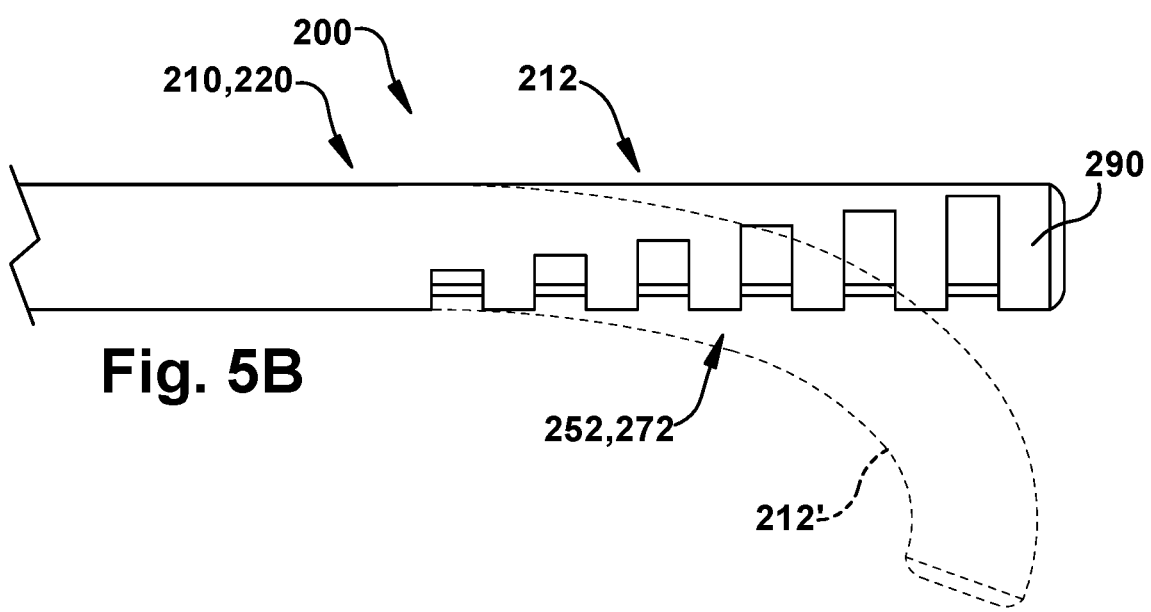

For example, cutouts with a constant depth and angular location, such as those illustrated in the configuration of FIGS. 1A-2D will assume a constant-curvature shape when the deflectable joint is actuated. As another example, Referring to FIG. 5B, the depth of the cutouts 252, 272 can be configured to get gradually deeper toward the tip 290. Because of this, when the deflectable tip 212 is actuated from the non-actuated condition (solid lines at 212) to the actuated condition (dashed lines at 212'), the curvature of the deflectable tip 212 increases toward the tip 290 of the device 220. This can be useful for applications in which "tip-first" bending is desired.

Figure 5C:
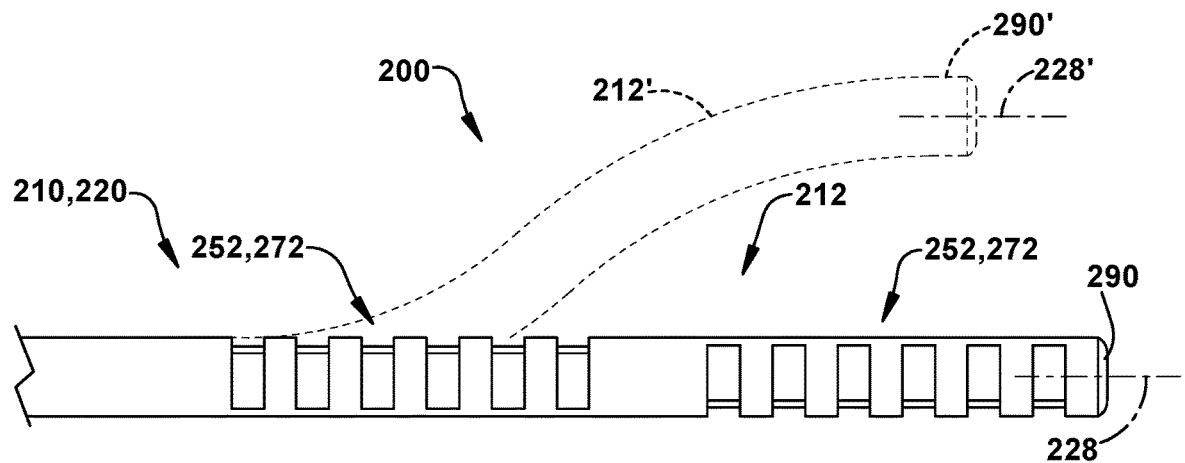

As another example, the cutouts 252, 272 can be rotated axially by 180 degrees at a predetermined position along the length of the deflectable joint 212. For example, as shown in FIG. 5C, a proximal half of the cutouts 252, 272 can be positioned facing one direction and the other distal half of the cutouts can be facing in the opposite direction. Because of this, when the deflectable tip 212 is actuated from the non-actuated condition (solid lines at 212) to the actuated condition (dashed lines at 212'), the proximal and distal halves curve in opposite directions, generating an s-shape which maintains the orientation of the tip 290. Thus, during actuation, the movement of the tip 290 can be purely translational, as illustrated at 290'. In this manner, the tip 290 translates while maintaining its orientation, i.e., the axis 228, 228' at the tip positions 290, 290' are parallel. This design can, for example, be useful in decoupling tip rotation from tip translation so that manual or robotic control is simpler and more intuitive.

Figure 5D:
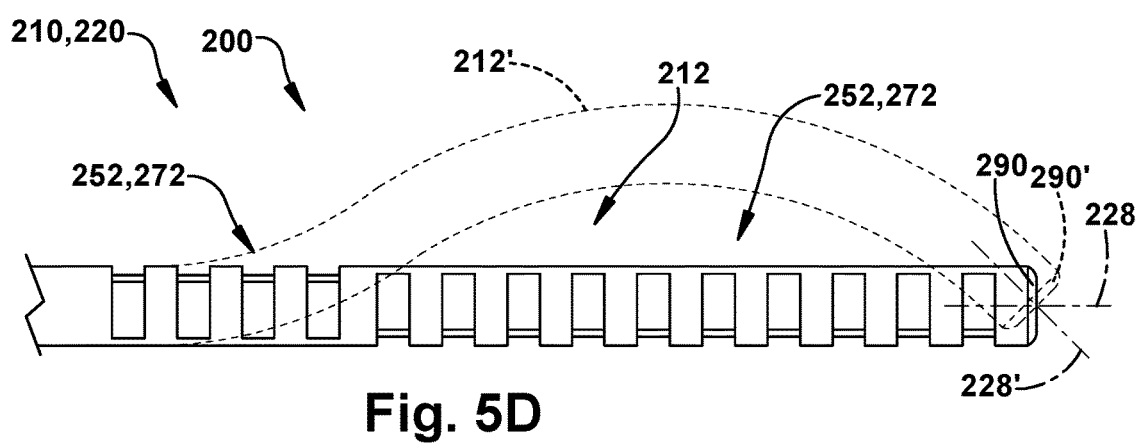

The cutouts 252, 272 can also be configured to help provide specific shapes and motion of the deflectable tip 212. Referring to FIG. 5D, the 180 degree rotated cutouts 252, 272 can configured to permit a purely bending movement at the tip 290. In this configuration, the proximal cutouts 252, 272 can form a smaller portion (i.e., less than half) of the total number of cutouts, such as about 30%. Because of this, when the deflectable tip 212 is actuated from the non-actuated condition (solid lines at 212) to the actuated condition (dashed lines at 212'), the proximal and distal portions curve in opposite directions. Because the proximal cutouts 252, 272 form a disproportionally small percentage of the total number of cutouts, the distal portion can curve opposite the proximal portion to maintain the translational position of the tip 290. As a result, during actuation, the tip 290 rotates in a manner such that the axis 228 at the tip rotates or pivots about a point, as illustrated generally at 228 and 228'. Thus, during actuation, the movement of the tip 290 can be purely rotational, with the bending angle at the tip rotating as illustrated at 290' while maintaining its lateral position. In this configuration, there is no lateral displacement within the bending plane at the tip 290. As with the configuration of FIG. 5C, the configuration of FIG. 5D can also be useful in decoupling tip translation from rotation so that manual or robotic control is simpler and more intuitive.

In another example configuration, the cutouts 252, 272 can be rotated about the axis 228 gradually along the length of the deflectable joint 212. In this example configuration, the actuated shape of the deflectable joint 212 will be helical.

In another example configuration, the depths cutouts 252, 272 can be configured to become gradually shallower toward the tip. In this configuration, the passive strength of the deflectable joint 212 with respect to external loads can be increased.

Additionally, the shape or profile of the cutouts 252, 272 themselves can be configured to help address or alleviate structural issues that can arise regarding the deflectable joint 212. For example, shapes such as circular, V-shaped, U-shaped, dogbone, parabolic, etc. can be used to help avoid stress concentrations, cracks, material fatigue, etc.

Advantageously, the cutouts 252, 272 can be configured in any of the manners described in the preceding paragraphs in order to conform to a patient-specific or procedure-specific anatomy. Generally speaking, the cutouts 252, 272 can be designed to conform to any class of desired shapes, such as those defined by patient anatomy or procedural requirements.

Multiple Deflectable Tube Devices

Figure 6:
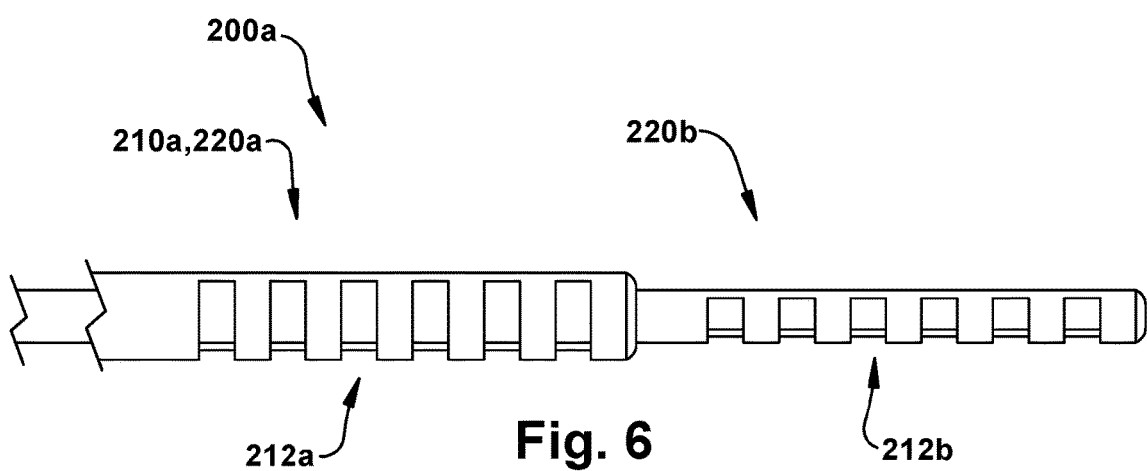
FIG. 6 illustrates an implementation including two concentric tube structures with small diameter bendable tips.

Advantageously, the modular design of the deflectable tube device 220, providing an unobstructed lumen 226, allows for multiple devices, each possessing a deflectable joint 212, to be deployed. For example, as shown in FIG. 6, an example configuration of a surgical tool 210a includes two deflectable tube devices 220a and 220b. Each of the devices 220a, 220b includes a deflectable joint 212a, 212b, respectively. In the example configuration of FIG. 6, the deflectable joints 212a, 212b are deflectable tips. Either or both of the deflectable joints 212a, 212b could, however, be positioned at any desired location along the length of its corresponding deflectable tube device 220a, 220b.

As shown in FIG. 6, the nested configuration of the surgical tool 210a allows for selectively bending the devices 220a, 220b. Since the inner device 220b is constructed of a flexible material (e.g. nitinol), it will follow the curve of the outer device 220a and extend from the distal end of the outer device. Since the outer device 220a is also constructed of a flexible material, the curvature of the deflectable joint 212a can be affected by the inner device 220b extending through it. The larger diameter of the outer device 220a can help minimize this affect. The configuration of the outer device 220a can also be designed/selected to help minimize this effect. For example, the outer device 220a can be constructed with tubes having a greater wall thickness or can be configured with a different cross-section, such as a hexagonal cross section.

Advantageously, the surgical tool 210a of FIG. 6 provides an increase in the degrees of freedom and the size/extent of the workspace in which the tool can operate. The surgical tool 210a of FIG. 6, for example, provides six degrees of freedom—axial translation, rotation about the axis, and bending at the deflectable joint, for each of the deflectable tube devices 220a, 220b that make-up the tool 210a. Additional degrees of freedom can be added via further deflectable tube devices, with or without deflectable joints outside the two-device tool 210a of FIG. 6. Additional degrees of freedom can also be realized through the deployment of a surgical instrument through the inner lumen 226b of the inner device 220b.

Flexible Transmission Segment

Referring to FIGS. 7A-E, a surgical tool 210 can include a flexible transmission segment 300 on each tube 222, 224 of the deflectable tube device 220. The transmission segment 300 is configured to be flexible in bending (and symmetrically so), but still relatively stiff in the axial direction and in torsion. This can be done in a variety of manners, such as by forming the transmission segment 300 of a flexible material, such as plastic, in order to provide adequate bending properties, and then reinforcing the segment to provide the desired axial strength and torsional stiffness. Reinforcing a plastic transmission segment can be done, for example, by embedding reinforcing fibers in the structure of the transmission segment 300, or by embedding members, such as wires, in a predetermined pattern, such as a helical or meshed pattern.

Another manner in which to configure the transmission segment 300 is illustrated in FIGS. 7A-7E. In this configuration, the transmission segment 300 includes a series of slits 302, pairs of which extend toward each other into opposite sides of the tubes 222, 224. Each pair of slits 302 is rotated 90 degrees from the pairs of slits adjacent to it. As a result, the pairs of slits 302 are arranged in an alternating pattern in which they extend into the tubes 222, 224 in directions that are perpendicular to each other, from pair to adjacent pair.

The transmission segments 300 define portions of the tubes 222, 224 that are very flexible in bending the directions in which the slits 302 extend. Therefore, every other pair of slits 302 permits bending in one bending plane, while the slit pairs in between permit bending in another perpendicular bending. Together, the pairs of slits 302 permit bending of the transmission segment 300 in any direction. Advantageously, while the flexible transmission segments 300 reduces the bending stiffness of the tubes 222, 224 to permit this bending, the torsional and axial stiffness of the transmission segments is maintained relatively high. To enhance the torsional and axial stiffness, in a plastic or polymer configuration of the device 220, fiber reinforced materials could be used in the construction of the transmission segments 300.

Those skilled in the art will appreciate that, much like the cutouts of the deflectable portions 250, 270, the flexure characteristics of the transmission segments 300 can be implemented in the tubes 222, 224 in manners other than through the implementation of the slits 302. For example, in a plastic implementation, the flexure characteristics of the transmission segments 300 can be implemented through the use of different plastic materials along the lengths of the tubes 222, 224. Flexure characteristics of the transmission segments 300 can also be implemented through material variations within the cross section of the tubes 222, 224, or by varying the wall thicknesses of the tubes.

Figure 7E:
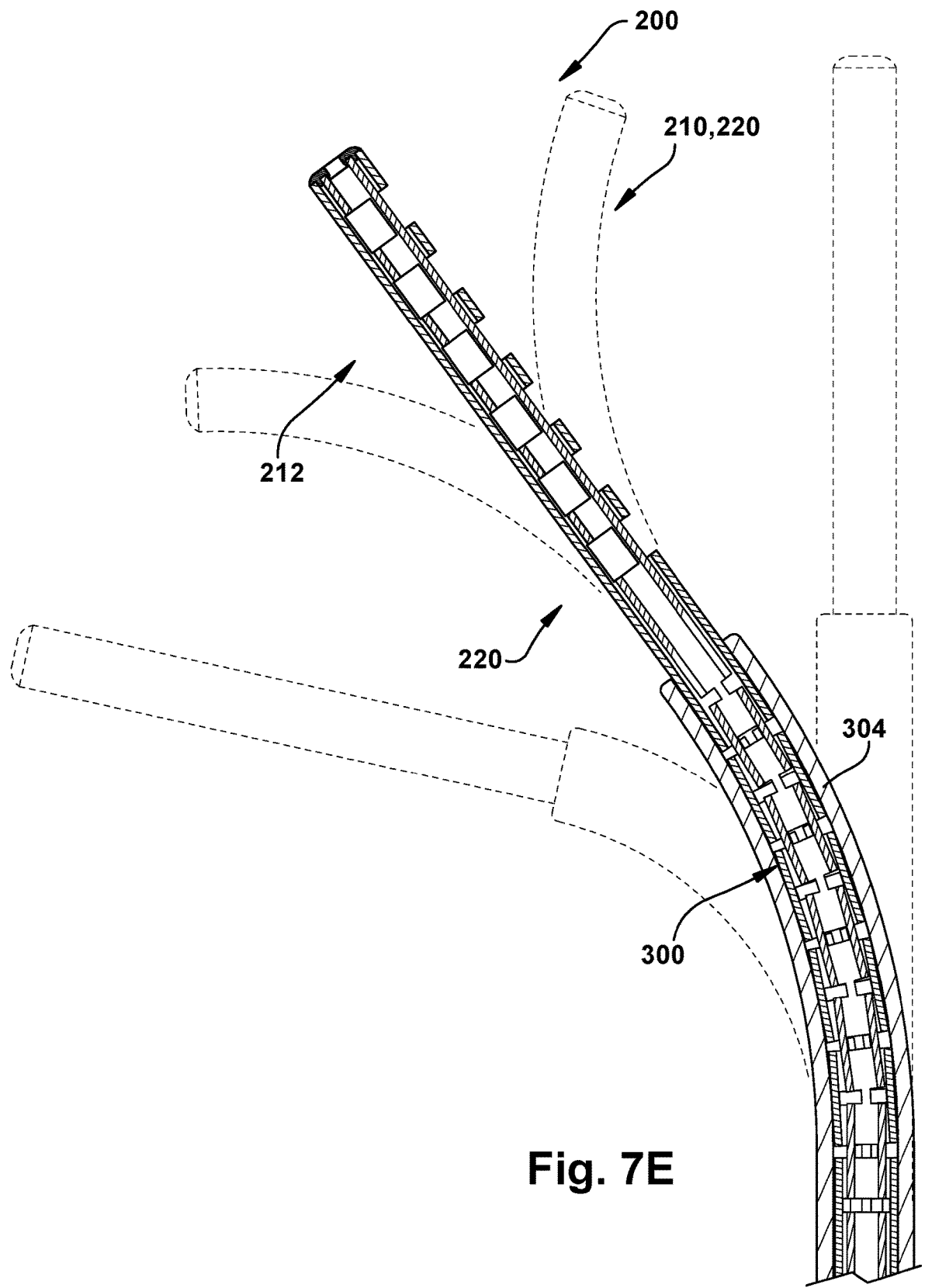

In the assembled condition of the device 220, the flexible transmission segments 300 of the inner and outer tubes 222, 224 are aligned with each other axially along their respective lengths. Referring to FIG. 7E, the device 220 can be positioned in another device 304, such as a pre-curved tube, a flexible endoscope, or a deflectable tip of another deflectable tube device, with the transmission segments coinciding with a curve in the device. Advantageously, the transmission segments 300 are configured to render the device 220 non-interacting with the device 304 in which it is positioned. By "non-interacting," it is meant that, due to the enhanced flexibility of the transmission segments 300, actuation and rotation of the device 220 will not affect the position or motion of the outer device 304. Similarly, due to the enhanced flexibility of the transmission segments 300, the ability of the device 220 to actuate its deflectable tip 212 is unaffected by the curvature or motion of the outer device 304.

Any motion of the deflectable tip 212 that would impart unwanted movement to the outer device 304 is absorbed or taken-up by the transmission segments 300. Similarly, any motion of the outer device 304 that would impart unwanted movement to the device 220, especially the deflectable tip 212, is also absorbed or taken-up by the transmission segments 300. It can therefore be seen that the transmission segments 300 can be positioned to de-couple the motion of the device 220 from structures in which it is positioned.

It can also be seen that, advantageously, the flexible transmission segments 300 also enables deployment of a deflectable tube device 220 along a curved path without affecting its ability to actuate its deflectable tip. This can be advantageous, for example, where the deflectable tube device is deployed through a curved delivery device, such as a flexible endoscope or a deflectable tube device. This can be especially advantageous in procedures such as minimally invasive procedures and Natural Orifice Transluminal Endoscopic Surgeries (NOTES).

Configurations with More than Two Tubes

The deflectable tube device 220 can include more than two concentric tubes. For instance, referring to FIGS. 8A and 8B, an example configuration of the deflectable tube device 320 can include three tubes: an inner tube 322, a middle tube 324, and an outer tube 326. The functions of the tubes 322, 324, 326 depends on the arrangement of the tubes themselves, i.e., the radial directions in which their respective deflectable portions face. To this end, the tubes 322, 324, 326 can be configured to enhance either the dexterity of the deflectable tube device 320 or to reinforce the device to increase stiffness and avoid tube buckling.

To enhance the dexterity of the deflectable tube device 320, the tubes 322, 324, 326 can be rotated relative to each other so that their respective deflectable portions face along a bending plane in which bending is desired. Thus, in the configuration illustrated in FIGS. 8A and 8B, the deflectable tube device can be configured to bend along three different bending planes, one for each tube in the structure. In this configuration, bending along one of the bending planes can be achieved by pulling simultaneously on the other two tubes. The pull forces applied by the tubes will cause the remaining tube to bend along the bending plane through or along which its deflectable portion faces.

The deflectable tube device 320 thus operates in a manner identical to the operation of the two-tube structures described herein, except that actuation is achieved by pulling on two tubes instead of one. To cause the deflectable tube device 320 to bend in the bending plane of the inner tube 322, a pulling force is applied by the middle tube 324 and the outer tube 326. Similarly, to cause the deflectable tube device 320 to bend in the bending plane of the middle tube 324, a pulling force is applied by the inner tube 322 and the outer tube 326. Finally, to cause the deflectable tube device 320 to bend in the bending plane of the outer tube 326, a pulling force is applied by the inner tube 322 and the middle tube 324.

To reinforce the device to increase stiffness and avoid tube buckling, two out of the three tubes 322, 324, 326 can be configured to bend in the same or similar bending plane. For example, as shown in the configuration illustrated in FIG. 8A, the outer tube 326 can be used in a redundant manner to enforce the bending imparted by middle tube 324. The outer tube 326 is positioned so that its cutouts face in the same direction as the cutouts in the middle tube 324. The tubes 324, 326 together provide increased torsional stiffness and axial strength while at the same time providing actuatable bending in the same bending plane.

Rotational Tip Connection

Figures 9A, 9B:
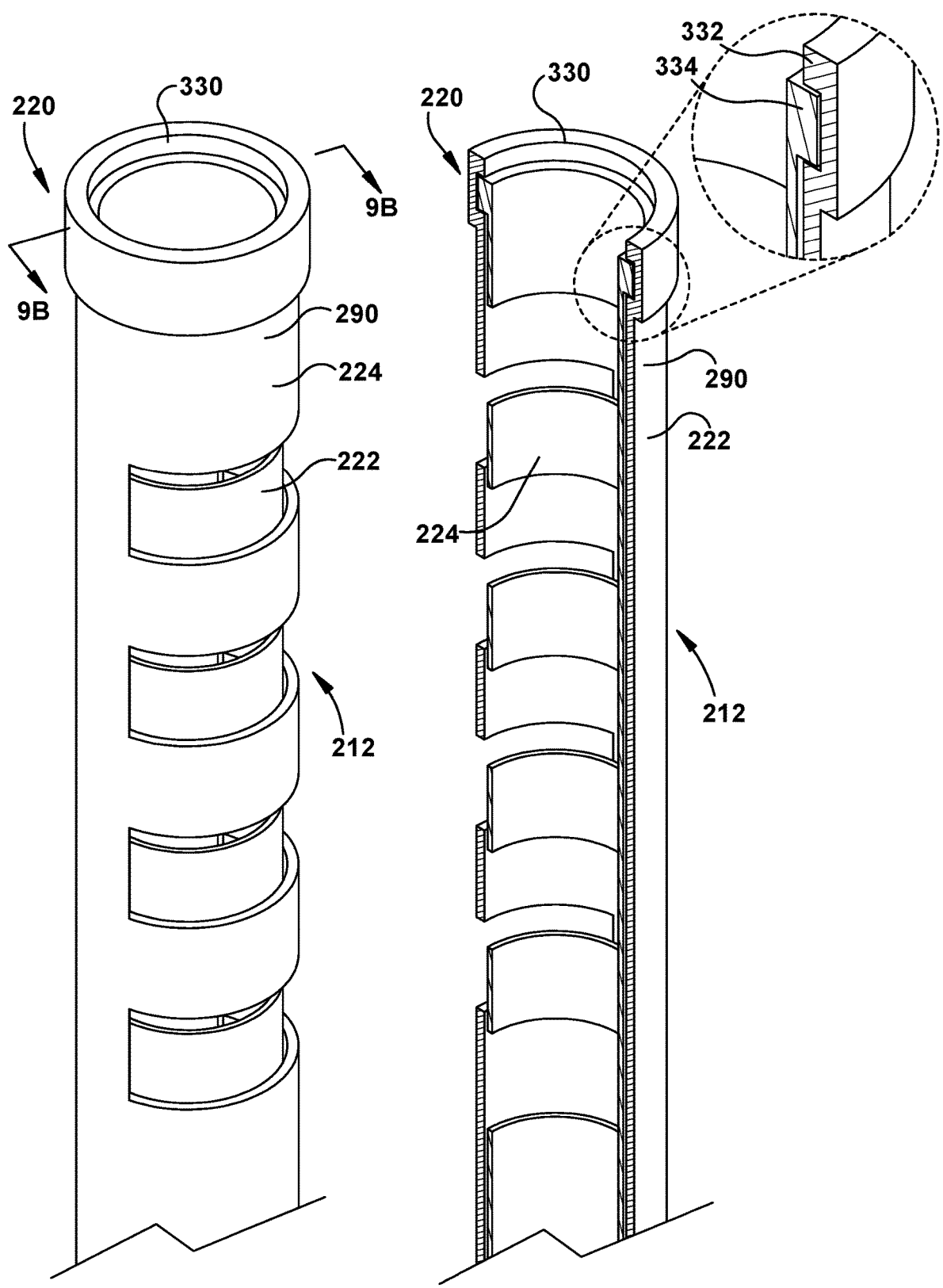

Referring to FIG. 9A-B, the deflectable tube device 220 can include a bearing tip 330 at the distal end 290 of the structure. The bearing tip 330 can both connect the tubes 222, 224 so that relative push/pull movement between the tubes causes the deflectable joint 212 to bend as described above, and also so that the tubes can rotate freely relative to each other. As such, the bearing tip 330 includes an outer bearing component 332 fixed to the outer tube 222 and an inner bearing component 334 fixed to the inner tube 224. The bearing components 332, 334 have a bearing interface that promotes free rotation between the components and the attached tubes 222, 224, while fixing their relative axial positions.

Referring to FIG. 9C-D, the deflectable tube device 220 can include a pinned tip connection 340 at the distal end 290 of the structure. The pinned tip 340 can both connect the tubes 222, 224 so that relative push/pull movement between the tubes causes the deflectable joint 212 to bend as described above, and also so that the tubes can rotate freely relative to each other. As such, the pinned tip 340 includes a slot 342 in the distal end of the outer tube 222 and one or more pins 344 fixed to the inner tube 224 and extending through the slot. The pin 344 can ride in the slot 342 when the tubes 222, 224 are rotated relative to each other and blocks relative axial movement between the tubes. The pinned tip 340 thus promotes free rotation between the tubes 222, 224, while fixing their relative axial positions.

Figure 8A:
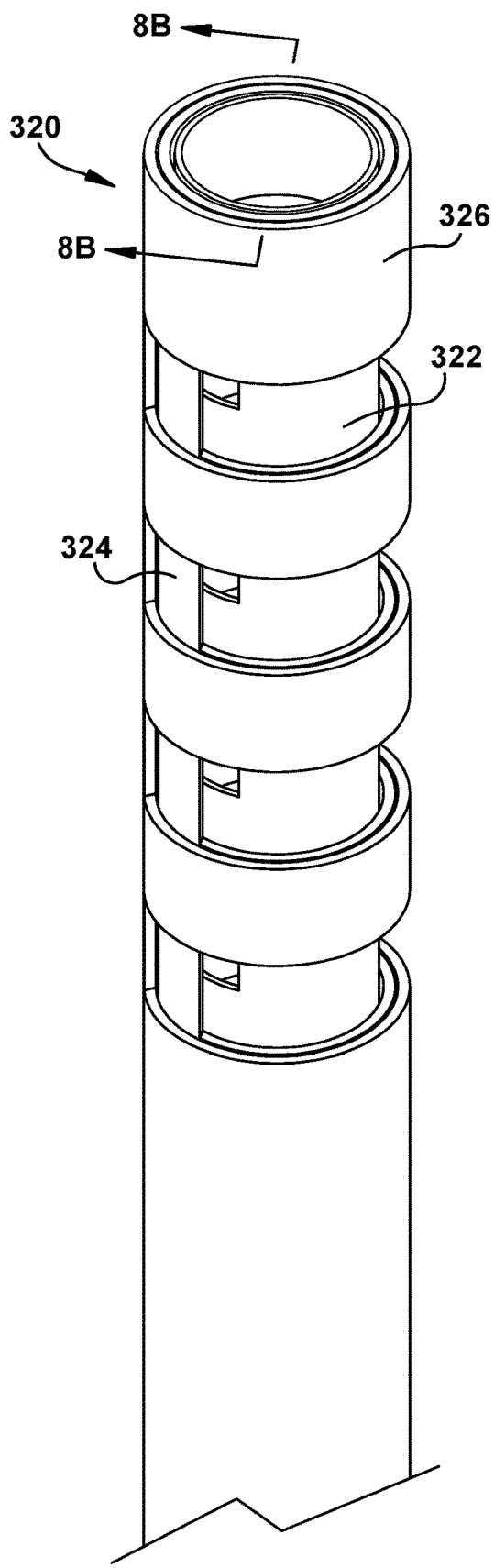
FIGS. 8A and 8B illustrate a variation on the concentric tube structure of FIGS. 1A and 1B including an additional concentric tube.
Figure 8B:
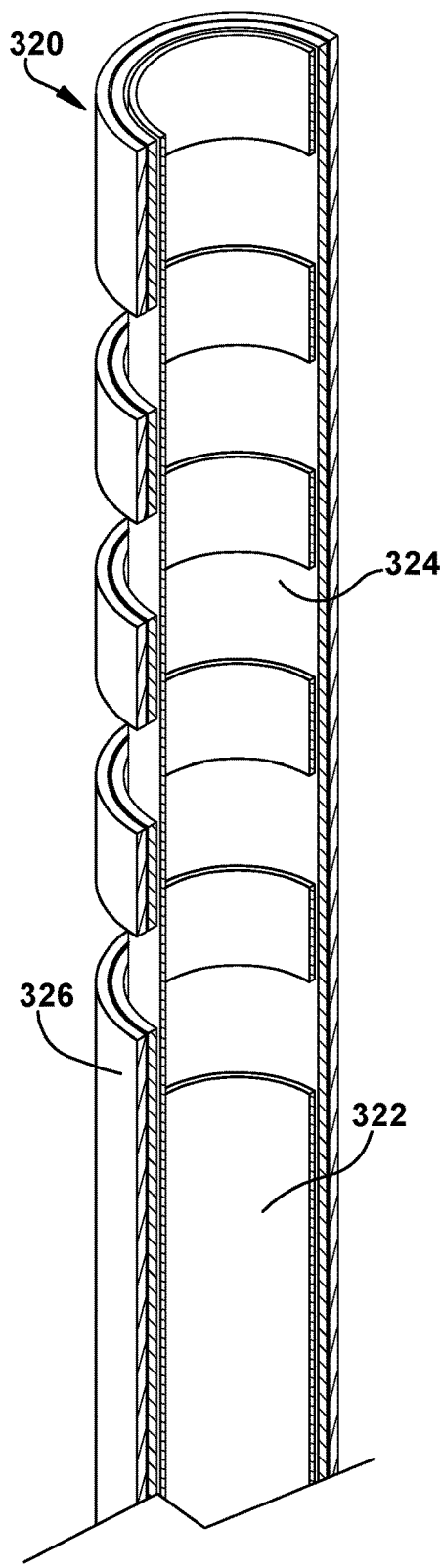

The rotational tip connections illustrated in FIGS. 9A-9D can also be beneficial in the embodiments of FIGS. 8A and 8B where the deflectable tube device 320 includes tubes in excess of two. By rotating the tubes 322, 324, 326 to desired positions relative to each other, the bending planes of the respective tubes can be selected. Because of this, the bending directions of the tubes 322, 324, 326 can be selected. Advantageously, this can allow for selecting the multiple actuation directions of the deflectable tube device 320 and also selecting which of the tubes 322, 324, 326 reinforce each other torsionally and axially. Additionally, with a rotational tip connection, these purposes can be selected/configured in real time while the device 320 is used.

Manual Actuation Handle

The deflectable tube device 220 implementing a deflectable joint 212 can implement robotic control, manual control, or a combination of robotic and manual control. Example configurations of manual actuators are illustrated in FIGS. 10A-B and 11A-B.

In the configuration of FIG. 10A-B, a control handle 350 includes a housing 362 that supports a gear and rack mechanism 352. The gear and rack mechanism 352 includes an actuator gear 354 that is rotatable manually by the user, for example, via a knob 360 positioned outside the housing 362. As another example, the control handle could be configured to rotate the gear 354 through rotation of the handle itself. Rotation of the gear 354 imparts axial movement in two racks 356, 358, each of which is connected to one of the inner and outer tubes of the deflectable tube device 220. In the illustrated configuration, the first rack 356 is connected to the outer tube 222 and the second rack 358 is connected to the inner tube 224.

In operation, clockwise rotation (as viewed in FIG. 10B) of the gear 354 causes the first rack 356 and the outer tube 222 to move in a first direction, indicated generally by arrow A in FIG. 10B, and the second rack 358 and inner tube 222 to move in a second direction, opposite the first direction, indicated generally by arrow B. Counterclockwise rotation of the gear 354 causes the first rack 356 and the outer tube 222 to move in the second direction (arrow B), and the second rack 358 and inner tube 224 to move in the first direction (arrow A).

The user can rotate the device 220 simply by rotating the handle 350 and can insert/retract the device simply though push/pull movement of the handle. The user can actuate the deflectable joint 212 by rotating the actuator gear 354, e.g., via a control knob 360. Where the deflectable joint is a deflectable tip 212 carrying an end effector, the effector can be used to perform a surgical task through a combination of gross tool movement via handle 350 movement and joint actuation via the gear and rack mechanism 352.

Advantageously, the gear and rack mechanism 352 imparts relative axial movement to both the inner tube 224 and the outer tube 222 simultaneously. This increases the motion scaling of the device 220, i.e., the amount of tip 212 deflection in response to knob 360 turning. This motion scaling can be tailored by selecting the gearing of the actuator gear 354 and racks 356, 358. The gearing can also be configured to provide a mechanical advantage that allows the user to actuate the tip 212 with very little effort, thus allowing him/her to achieve delicate operation. In the configuration of FIGS. 11A-B, an actuator handle 380 includes a rotatable wheel 382 to which the tubes 222, 224 are connected, for example, via respective pins or other fasteners. The outer tube 222 is connected to the outer circumference of the wheel 382 at a first location on the wheel (shown in dashed lines in FIG. 11B). The inner tube 224 is connected to the outer circumference of the wheel 382 at a second location diametrically opposite the first location.

The wheel 382 rotates on a shaft 384, which is supported on a housing 390 of the handle 380. The shaft 384 extends outside the housing 390 where it is connected to an actuator handle 386. Rotation of the actuator handle 386 therefore imparts rotation to the wheel 382 via the shaft 384. In use, the operator can grasp the device handle 380 to manipulate the device 220 axially and rotationally. To actuate the deflectable tip 212, the user rotates the actuator handle 386 to impart rotation to the wheel 382.

Rotation of the wheel 382 imparts axial movement to the tubes 222, 224. In the illustrated configuration, clockwise rotation of the wheel 382 causes the inner tube 224 to move in a first direction, indicated generally by arrow A in FIG. 11B, and the outer tube 222 to move in a second direction, opposite the first direction, indicated generally by arrow B in FIG. 11B. Counterclockwise rotation of the wheel 382 causes the inner tube 224 to move in the second direction, and the outer tube 222 to move in the first direction.

Control Handle with Clutch

Figure 12A:
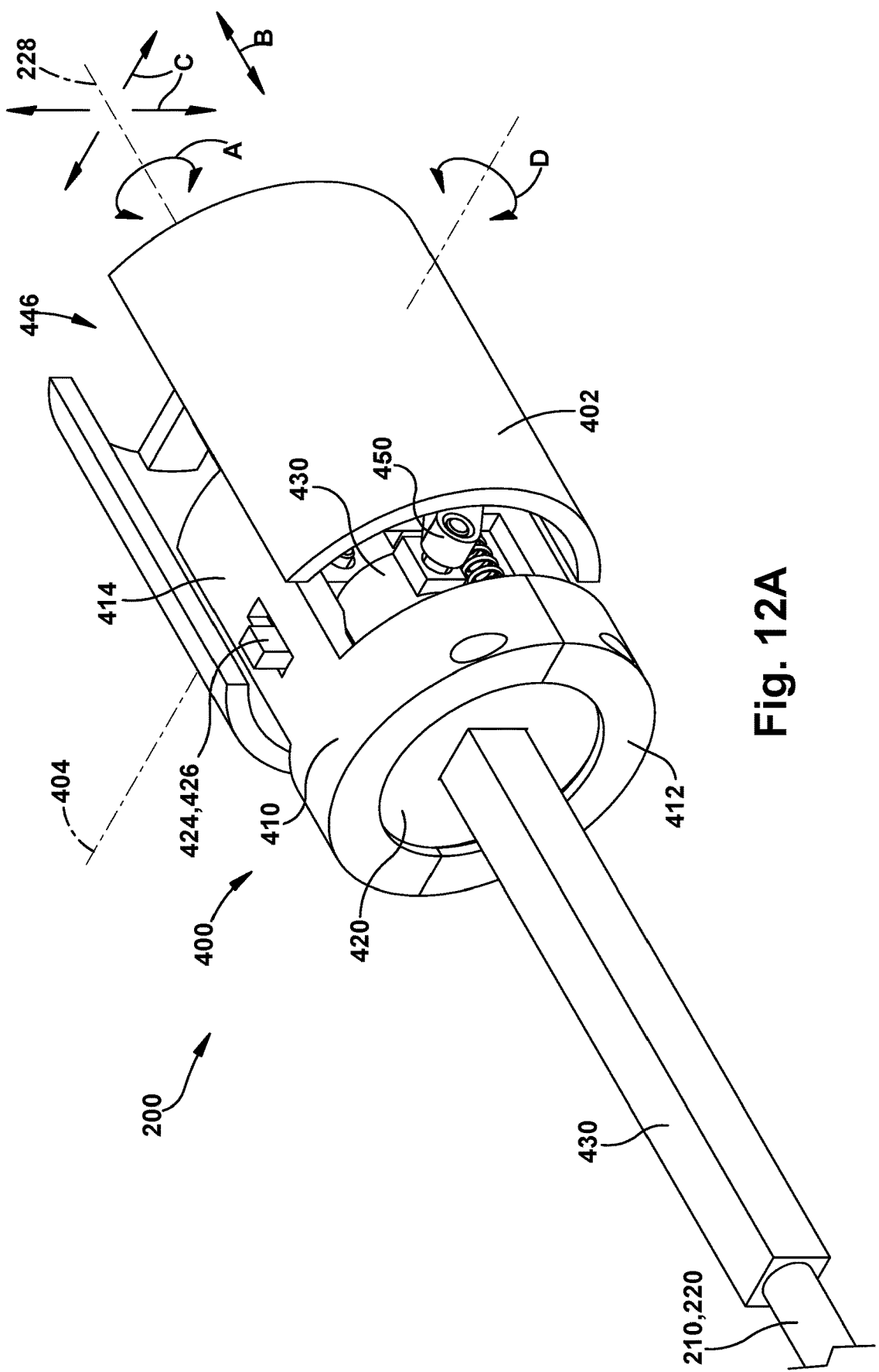
FIGS. 12A and 12B illustrate another control handle for the concentric tube structure, including a clutch mechanism.
Figure 12B:
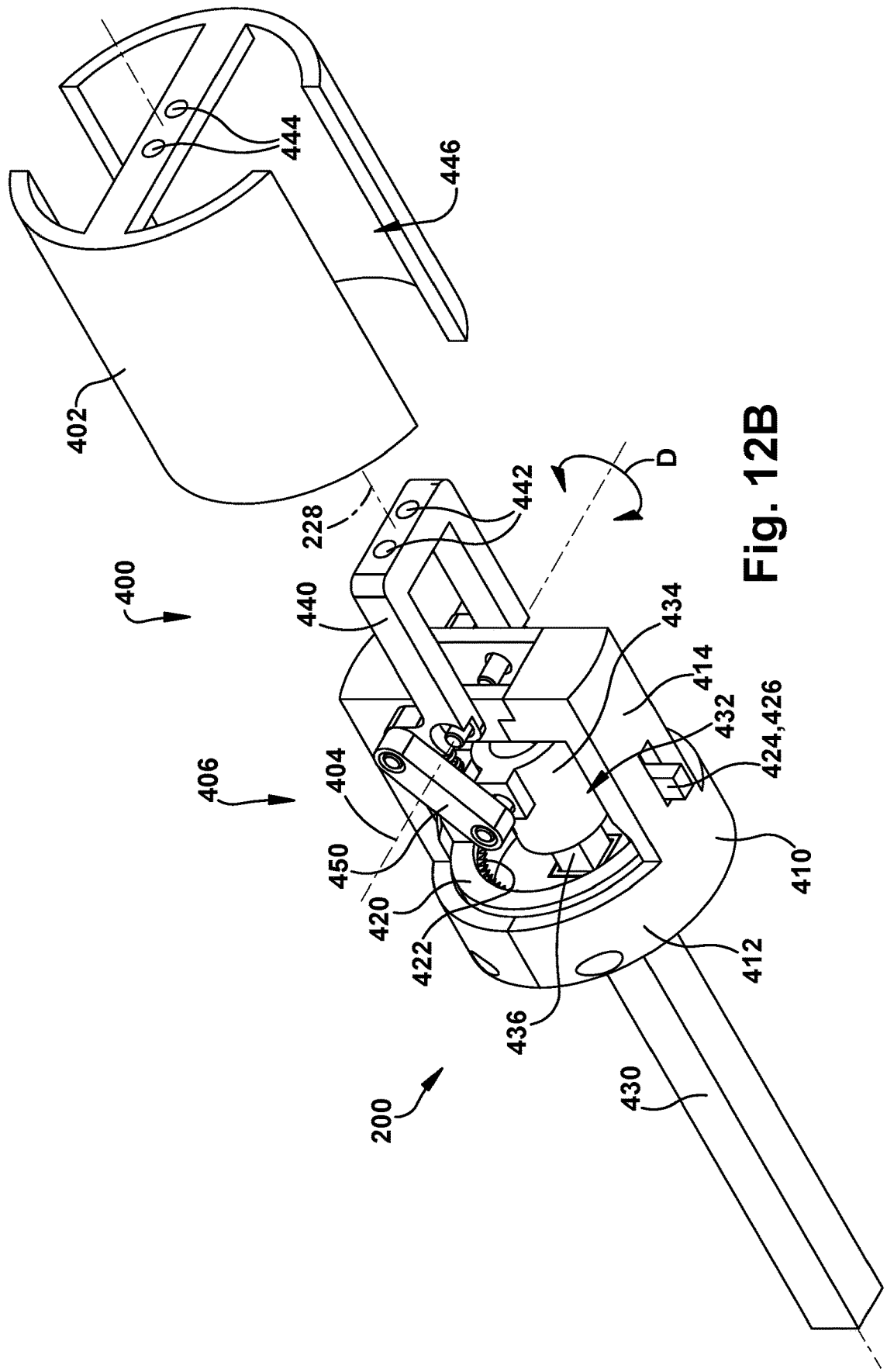

Referring to FIGS. 12A-B, in a manually operated configuration of the surgical system 200, the surgical tool 210 can be connected to a control handle 400. The control handle 400 includes a cover 402 that serves as a handle for the user to grasp in order to manipulate the surgical tool. While the cover 402 is illustrated as having a generally cylindrical configuration, alternative configurations, such as an ergonomically contoured configuration, could be implemented.

The control handle 400 facilitates gross manipulation of the surgical tool 210, i.e., the deflectable tube device 220, by grasping the cover 402 and moving the system 200 as a whole. In doing so, the user can rotate the device 220 about the axis 228 (see arrow A), translate the device along the axis (see arrow B), and can adjust the attitude of the device, i.e., adjust the position of the axis itself (see arrow C). Additionally, the cover 402 can be pivoted about an actuator axis 404 (see arrow D) in order to actuate the deflectable joint/tip 212, which is described in detail below with respect to FIGS. 13A-C.

Referring to FIG. 12B, the control handle 400 includes an actuator mechanism 406 including a frame 410 with a circular base 412 and a rectangular lever support 414. The base 412 supports a circular race 420 in a manner such that the race can rotate relative to the base about the tool axis 228. The race 420 includes gear teeth 422 that extend annularly around an inner surface of the race. The lever support 414 supports a pair of pawls 424 that are spring biased to engage the gear teeth 422 and lock the base 412 and race 420 to prevent their rotating relative to each other. The pawls 424 include actuator buttons 426 positioned radially opposite each other on the lever support 414 and can be actuated by pulling the buttons against the spring bias to disengage the pawls from the gear teeth 422 and permit relative rotation of the race 420 relative to the base 412/frame 410. In this manner, these components form a clutch 428 for engaging and disengaging the frame 410 from the race 420.

The control handle 400 also includes an outer tool support 430 that is connected to the race 420 and is configured to receive the deflectable tube device 220 and to connect to the outer tube 222 of the device. The control handle 400 also includes a tool actuator 432 that includes a cylindrical sleeve 434 and an inner tool support 436 that extends into the outer tool support 430 and connects with the inner tube 224 of the device 220. The inner tool support 436 is connected to the sleeve 434 in a manner such that the inner tool support can rotate relative to the sleeve about the axis 228. The inner tool support 436, having a square cross-section that mates with an inner surface of the outer tool support 430 so that the inner tool support rotates about the axis 228 in response to rotation of the outer tool support. The tool actuator 432 is actuatable to move axially relative to the frame 410 such that the inner tool support 436 can translate axially relative to the outer tool support 430.

The control handle 400 also includes an actuator lever 440 that is connected to the frame 414 and extends from the rear of the handle, opposite the device 220. The lever 440 is connected for pivotal movement about the actuator axis 404. The lever 440 includes fastener receiving apertures 442 that correspond to apertures 444 in the cover 402 so that the cover can be connected to the lever. In use, pivotal movement of the lever 440 can be effectuated through pivotal movement of the cover 402. To facilitate this, the cover 402 includes slots 446 that provide clearance for the frame 414 and also permit user access to the pawl buttons 426. The lever 440 has a generally L-shaped configuration with the pivot axis extending through the intersection of its legs. The longer leg of the L-shaped lever 440 is connected to the cover 402.

Figure 13A:
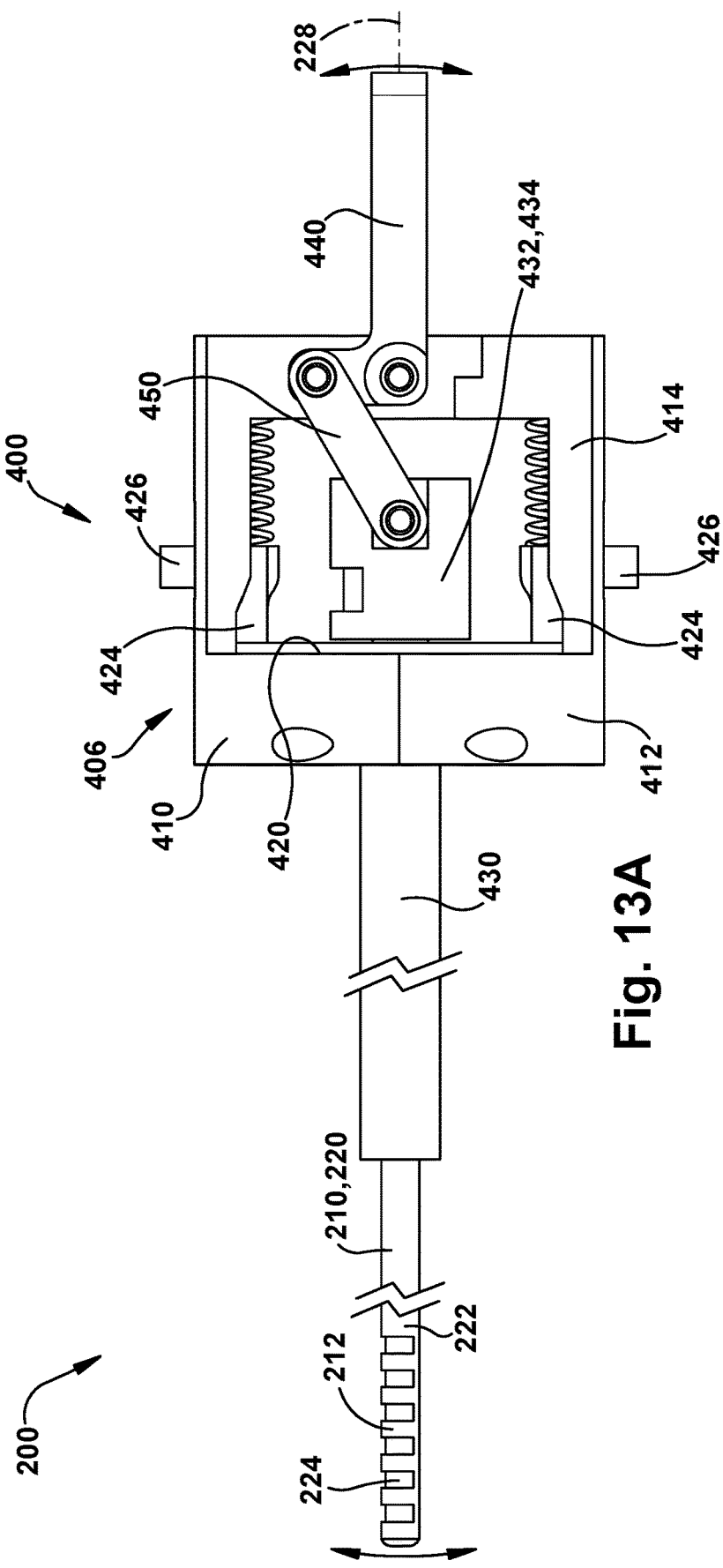
FIGS. 13A-13C illustrate the operation of the control handle including the clutch mechanism.

The control handle 400 also includes a linkage 450 that has a first end pivotally connected to the shorter leg of the L-shaped lever 440 and an opposite second end pivotally connected to the tool cylindrical sleeve 434 of the tool actuator 432. Through this linkage 450, rotational/pivoting actuation of the lever 440 effects linear translational movement of the tool actuator 432 along the axis 228. Referring to FIG. 13A, in a neutral position of the lever 440, the inner tool support 434 is positioned relative to the outer tool support 430 such that the deflectable tip 220 is maintained in an unactuated, i.e., straight configuration.

Figure 13B:
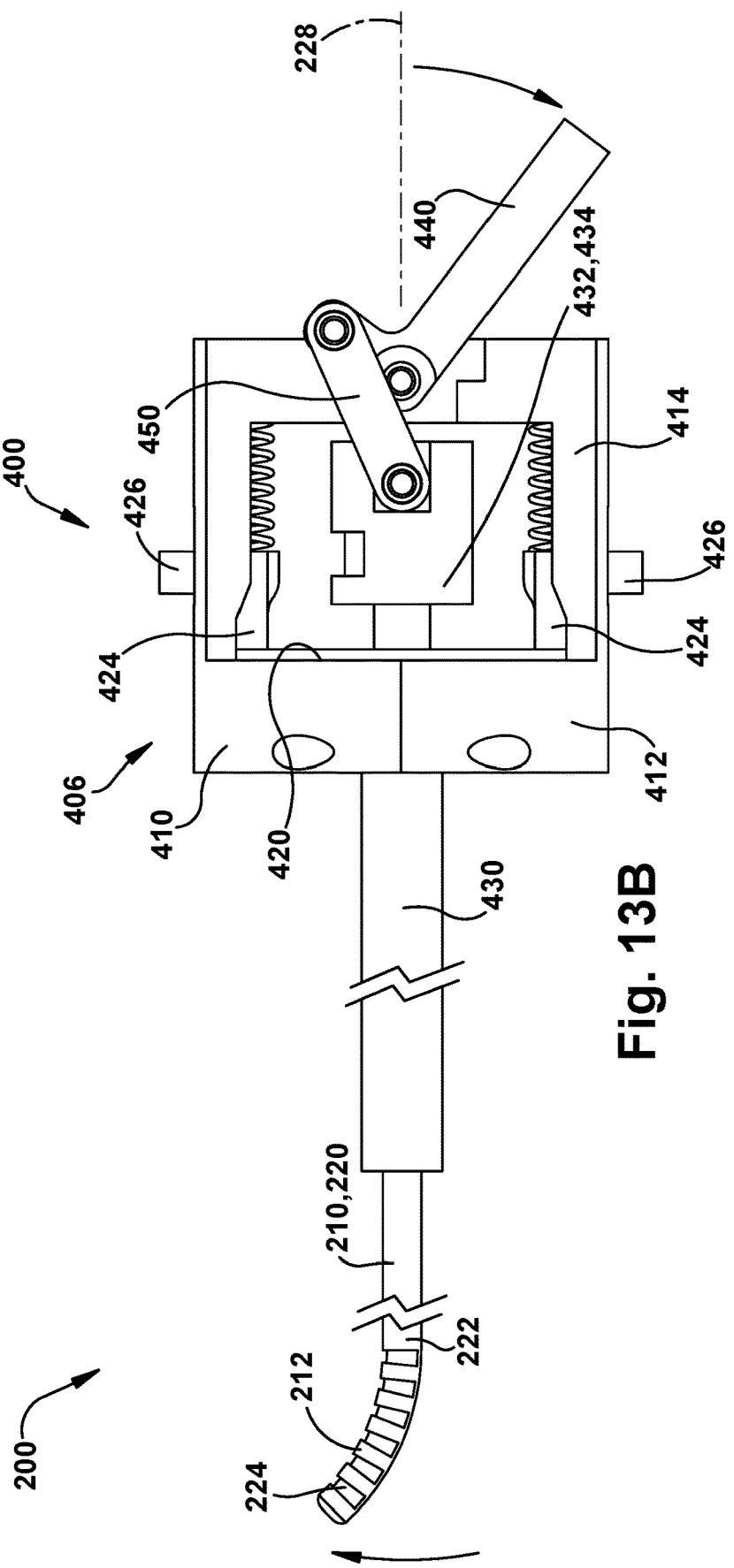

Pivoting the lever 440 downward to the position of FIG. 13B moves the tool actuator 432 to the right as viewed in the figures, which causes the inner tool support 434 to move to the right relative to the outer tool support 430. This causes rightward movement of the inner tube 224 relative to the outer tube 222 of the device 220, which actuates the deflectable tip 212 to bend upward as shown in FIG. 13B. Pivoting the lever 440 upward to the position of FIG. 13C moves the tool actuator 432 to the left as viewed in the figures, which causes the inner tool support 434 to move to the left relative to the outer tool support 430. This causes leftward movement of the inner tube 224 relative to the outer tube 222 of the device 220, which actuates the deflectable tip 212 to bend downward as shown in FIG. 13C.

Figure 13C:
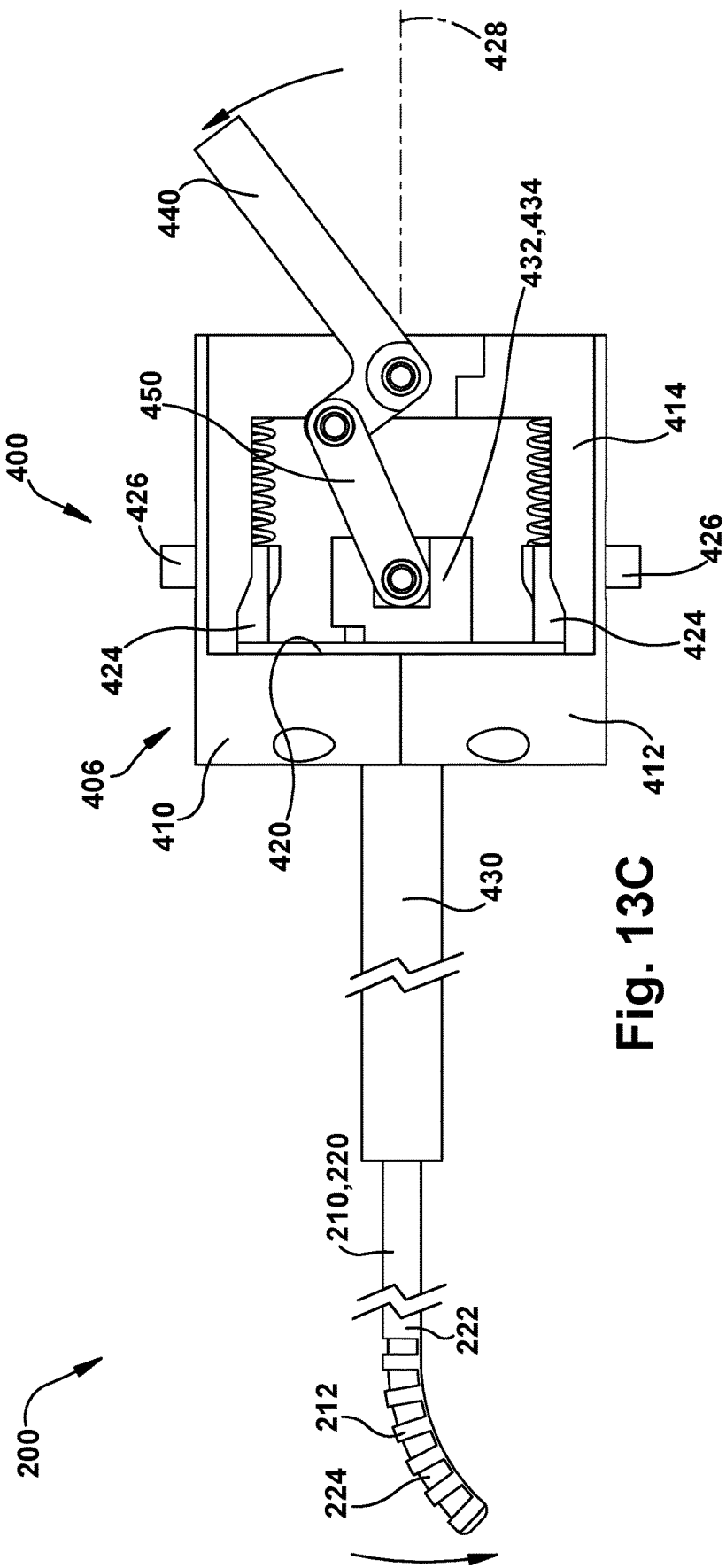

Because, as described above, the cover 402 is configured to pivot with the lever 440, the actuation movements shown and described in FIGS. 13A-C can be performed by manipulating the cover. Thus, grasping the control handle 400 by the cover 402, both gross movements of the surgical tool 210 and actuation movements of the deflectable tip 212 can be performed. Gross tool movements are performed by moving the entire control handle structure, while the actuation movement of the deflectable tip 212 are performed conveniently by pivoting the user's wrist to pivot the cover 402/lever 440.

Those skilled in the art will appreciate that gross movements of the surgical tool 210 can involve rotating the entire tool in order to adjust the bending plane of the deflectable tip 212. As a result, this can compromise hand-space/camera-space correspondence and thus make it difficult for the operator to intuitively actuate the tool 210 while viewing the workspace via a camera. Additionally, rotating the entire tool also can position the handle such that the actuator axis 404 no longer coincides with permitting the user to actuate the cover 402/lever 440 through bending wrist motion.

Advantageously, the clutch 428 is actuatable to disengage the frame 410 from the race 420, which decouples the device 220 from the control handle 400 so that the rotational position of the handle can be adjusted without affecting the rotational position of the device. When the clutch 428 is disengaged, the race 420 and the outer tool support 430 are disengaged from the frame 410 and therefore do not rotate with the handle. Since rotation of the inner tool support 436 is tied to rotation of the outer tool support 430, and since the sleeve 434 is configured to rotate relative to the inner tool support, the inner tool support and sleeve also do not rotate with the handle. Actuation of the clutch 428 therefore decouples the device 220 rotationally from the handle.

When the clutch 428 is engaged, the pawls 424 re-engage the gears 422 on the race 420, thereby re-coupling the race and outer tool holder 430 to the frame 410. The race 420 and outer tool holder 430 thus rotate about the tool axis 228 with the control handle 400. Since the outer tool holder 430 rotates the inner tool holder 436, the inner tool holder is also re-coupled and rotates along with the control handle 400. Advantageously, since the sleeve 434 is rotatable relative to the inner tool holder 436, the rotational position of the frame 410 does not affect the ability of the control handle 400 to actuate the deflectable tip 212 through actuation of the lever 440, which moves the inner tube 224 relative to the outer tube 222 of the device 220.

The clutch 428, permitting rotation of the control handle 400 without affecting the rotational position of the device 220, advantageously helps the operator maintain hand-space/camera-space correspondence, as well as a position that is comfortable and allows for device actuation in response to a preferred intuitive hand/wrist motion. This also allows the user to adjust the holding position to match the field of view of a camera that can be viewed in tandem with the device so that movements in the user's hand space corresponds to similar movements in the camera space.

The surgical tool 200 provides surgeons better control of the movement of the device 220 when inside an endoscope or working within a body cavity. This can be helpful in a variety of surgical applications. For example, this can be helpful in throat surgery for the removal of vocal folds or polyps. The surgical tool 200 can also be used for tool deployment, such as needle puncture through the abdominal wall to difficult-to-reach locations. One such difficult-to-reach location can, for example, be the lower calyces of the kidney. The surgical tool can also be useful in natural orifice procedures, for example, to access many hard to each areas of the abdomen with minimal patient trauma.

We claim:

1. A surgical system for manipulating tissue at a surgical site, comprising:
    an endoscope configured to be inserted and manipulated to position at a surgical site; and
    a nested tube structure that extends through an inner lumen of the endoscope, and has a distal end portion that exits the inner lumen to access the surgical site;
    wherein the nested tube structure comprises a first tube including a tubular side wall and a deflectable portion in which a portion of the side wall is configured to have a stiffness that is lower than opposing portions, a second tube including a tubular side wall and a deflectable portion in which a portion of the side wall is configured to have a stiffness that is lower than opposing portions, and a connection between the first and second tubes at a location that is distal of the deflectable portions, the nested tube structure comprising an inner lumen that extends through the first and second tubes;
    wherein the first and second tubes are positioned so that their respective deflectable portions are at least partially aligned with each other axially, and so that the low stiffness portions of the first and second tubes face in radial directions that differ angularly from one another, the deflectable portions of the first and second tubes defining a deflectable joint that is actuatable to form a bend in the nested tube structure;
    wherein the first tube, second tube, and endoscope are configured so that the nested tube structure, supported by the endoscope with the bend positioned outside the inner lumen of the endoscope, is configured to support a surgical instrument extending through the inner lumen of the nested tube structure for tissue manipulation at the surgical site.

2. The surgical system recited in claim 1, wherein the deflectable joint is actuatable to bend in two or more directions.

3. The surgical system recited in claim 2, further comprising a control handle connected to the nested tube structure, the control handle including an actuator mechanism for actuating the deflectable joint.

4. The surgical system recited in claim 3, wherein the actuator mechanism comprises a lever that is pivotable to move the first tube axially relative to the second tube.

5. The surgical system recited in claim 3, wherein the actuator mechanism comprises a gear and rack mechanism comprising a central gear rotatable manually via a handle and first and second rack gears engaged with the central gear and movable in opposite directions in response to rotation of the central gear, wherein the first rack gear is connected to the second tube and the second rack gear is connected to the first tube, wherein rotation of the central gear via the handle moves the first and second tubes axially in opposite directions relative to each other.

6. The surgical system recited in claim 3, wherein the actuator mechanism comprises a central wheel supported on an axle and rotatable manually via a handle connected to the axle, wherein the second tube and the first tube are connected to an outer surface of the wheel at different circumferential positions, wherein rotation of the wheel via the handle moves the first and second tubes axially in opposite directions relative to each other.

7. The surgical system recited in claim 3, wherein the actuator mechanism comprises a clutch that decouples the control handle from the nested tube structure so that the control handle can be rotated relative to the nested tube structure.

8. The surgical system recited in claim 2, wherein the nested tube structure further comprises an additional nested tube that further defines the deflectable joint, the additional tube reinforcing one of the first and second tubes, the additional tube comprising a side wall having a deflectable portion in which a portion of the side wall is configured to have a stiffness that is lower than opposing portions of the side wall that at least partially align with the bendable portion of at least one of the first and second tubes.

9. The surgical system recited in claim 2, wherein the nested tube structure further comprises an additional nested tube that further defines the deflectable joint, the additional tube comprising a side wall having a deflectable portion in which a portion of the side wall is configured to have a stiffness that is lower than opposing portions of the side wall and a distal end connected to at least one of the first and second tubes.

10. The surgical system recited in claim 9, wherein the deflectable portion of the additional tube is at least partially aligned with the deflectable portion of at least one of the first and second tubes, the deflectable portion of the additional tube being actuatable to bend in the direction of the low stiffness portion of the additional tube.

11. The surgical system recited in claim 9, wherein the application of an axial pulling force on the additional tube relative to at least one of the first and second tubes causes the deflectable portion of the additional tube to deflect and bend in the direction of the low stiffness portion of the additional tube.

12. The surgical system recited in claim 9, wherein the tubes are configured such that the low stiffness portion of the additional tube is rotated relative to the low stiffness portions of the first and second tubes so that the bending plane of the deflectable portion of the additional tube bends is different than the bending planes of the deflectable portions of the first and second tubes.

13. The surgical system recited in claim 2, wherein the deflectable portions of the first and second tubes are defined by cutouts in the first and second tubes, wherein the cutouts of the first tube face in at least two different directions and the cutouts of the second tube face in at least two different directions, wherein the deflectable joint when actuated bends in at least two different directions that coincide with the directions of the cutouts.

14. The surgical system recited in claim 2, wherein the first and second tubes each further comprise a flexible transmission segment positioned proximally of the deflectable joint, wherein the transmission segment of each tube comprises a series of low stiffness regions of the first and second tubes that promote free bending with minimal impact on axial strength and torsional stiffness.

15. The surgical system recited in claim 14, wherein the low stiffness regions of the first and second tubes are formed by a plurality of slits that extend laterally into the tubes.

16. The surgical system recited in claim 15, wherein the slits extend into the first and second tubes in pairs that extend toward each other into opposing sides of their respective tubes, and wherein adjacent pairs of slits are rotated ninety degrees relative to each other about a longitudinal axis of the tubes.

17. The surgical system recited in claim 14, wherein the nested tube structure comprises an inner lumen configured to receive a surgical instrument in the form of an additional nested tube structure comprising a first tube and a second tube including deflectable portions that together define a deflectable joint actuatable to bend in opposite directions, wherein the position of the transmission segment is configured to coincide with the location of the deflectable joint of the additional nested tube structure.

18. The surgical system recited in claim 1, wherein the first and second tubes are configured such that:
the application of an axial pulling force on the first tube relative to the second tube causes the first tube to pull on the second tube at the connection, which causes the deflectable portion of the second tube to deflect and bend in the direction of the low stiffness portion of the second tube; and
the application of an axial pushing force on the first tube relative to the second tube causes the second tube to pull on the first tube at the connection, which causes the deflectable portion of the first tube to deflect and bend in the direction of the low stiffness portion of the first tube.

19. The surgical system recited in claim 18, wherein the tubes are configured so that the bending of the deflectable portion of the second tube in response to the pulling by the first tube exerts a bending force on the deflectable portion of the first tube, which causes the deflectable portion of the first tube to bend in the direction of the bend in the second tube.

20. The surgical system recited in claim 18, wherein the tubes are configured so that the bending of the deflectable portion of the first tube in response to the tension applied by the second tube exerts a bending force on the deflectable portion of the second tube, which causes the deflectable portion of the second tube to bend in the direction of the bend in the first tube.

21. The surgical system recited in claim 18, wherein:
the tubes are configured so that the axial pulling force on the first tube relative to the second tube can be applied by one or both of:
a) applying a pulling force on the first tube relative to the second tube, and
b) by applying a pushing force on the second tube relative to the first tube; and
the tubes are configured so that the axial pushing force on the first tube relative to the second tube can be applied by one or both of:
c) applying a pulling force on the second tube relative to the first tube, and
d) by applying a pushing force on the first tube relative to the second tube.

22. The surgical system recited in claim 1, further comprising a surgical instrument extending through the nested tube structure and exits the distal end of the nested tube structure, wherein the surgical instrument comprises a second nested tube structure comprising a first tube and a second tube including deflectable portions that together define a deflectable joint actuatable to bend in opposite directions, wherein the deflectable joint of the nested tube structure receiving the second nested tube structure is configured to manipulate the second nested tube structure through its actuation to impart an additional degree of freedom to the second nested tube structure.

23. The surgical system recited in claim 1, further comprising a surgical instrument extending through the nested tube structure and exiting the distal end of the nested tube structure, wherein the surgical instrument comprises at least one of curettes, grippers, surgical lasers, graspers, retractors, scissors, imaging tips, cauterizing tips, ablation tips, morcelators, knives/scalpels, cameras, irrigation ports, suction ports, needles, probes, and manipulators.

24. The surgical system recited in claim 1, wherein the first tube and the second tube have one of a round and polygonal cross-section.

25. The surgical system recited in claim 1, further comprising a surgical instrument connected to a distal end of the nested tube structure.

26. The surgical system recited in claim 25, wherein the surgical instrument comprises at least one of curettes, grippers, surgical lasers, graspers, retractors, scissors, imaging tips, cauterizing tips, ablation tips, morcelators, knives/scalpels, cameras, irrigation ports, suction ports, needles, probes, and manipulators.

27. The surgical system recited in claim 1, wherein:
the low stiffness portion of the first tube is formed by portions removed from the tubular sidewall of the first tube to form a plurality of cutouts; and
the low stiffness portion of the second tube is formed by portions removed from the tubular sidewall of the second tube to form a plurality of cutouts.

28. The surgical system recited in claim 27, wherein the cutouts of the first tube and second tube have depths that increase progressively from proximally to distally so that the bend of the deflectable portion becomes progressively sharp proximally to distally.

29. The surgical system recited in claim 27, wherein the cutouts of the first tube and second tube have depths that decrease progressively from proximally to distally so that the bend of the deflectable portion becomes progressively sharp distally to proximally.

30. The surgical system recited in claim 27, wherein the radial positions of the cutouts of the first tube and second tube rotate progressively from proximally to distally.

31. The surgical system recited in claim 1, further comprising a bearing tip at the distal end of the nested tube structure, the bearing tip comprising a first bearing component connected to the first tube and a second bearing component connected to the second tube, the first and second bearing components being connected to each other and having a bearing interface that promotes free rotation of the bearing components and the attached tubes while fixing their relative axial positions.

32. The surgical system recited in claim 1, further comprising a pinned tip connection at the distal end of the nested tube structure, the pinned tip comprising a slot in the second tube and a pin that is fixed to the first tube and projects radially outward through the slot, wherein the pin and slot interface each other to permit relative rotational movement of the first tube and the second tube while fixing their relative axial positions.

33. The surgical system recited in claim 1, wherein the material used to construct the first and second tubes facilitates a pre-curvature of at least one of the first and second tubes.

34. The surgical system recited in claim 1, wherein the nested tube structure is configured to have a pre-curved configuration and the endoscope is configured to constrain the nested tube structure to deflect away from its pre-curved configuration when positioned in the endoscope, wherein portions of the nested tube structure extending from the endoscope are configured to return to their pre-curved configuration.

35. The surgical system recited in claim 1, wherein the material used to construct the first and second tubes is a shape memory alloy.

36. The surgical system recited in claim 35, wherein the shape memory alloy is nitinol.

\* \* \* \* \*